United States Patent
Schleicher et al.

(10) Patent No.: US 8,224,460 B2
(45) Date of Patent: *Jul. 17, 2012

(54) ANCHORING UNITS FOR LEADS OF IMPLANTABLE ELECTRIC STIMULATION SYSTEMS AND METHODS OF MAKING AND USING

(75) Inventors: Brett Schleicher, Valencia, CA (US); Andrew DiGiore, Santa Monica, CA (US); Rafael Carbunaru, Valley Village, CA (US); Courtney Lane, Ventura, CA (US); Kristen N. Jaax, Santa Clarita, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/207,876

(22) Filed: Aug. 11, 2011

(65) Prior Publication Data

US 2011/0295330 A1 Dec. 1, 2011

Related U.S. Application Data

(63) Continuation of application No. 12/413,081, filed on Mar. 27, 2009, now Pat. No. 8,019,443.

(60) Provisional application No. 61/041,536, filed on Apr. 1, 2008.

(51) Int. Cl.
*A61N 1/00* (2006.01)
(52) U.S. Cl. .................................................. 607/117
(58) Field of Classification Search ................... 607/117
See application file for complete search history.

(56) References Cited

U.S. PATENT DOCUMENTS

| | | | |
|---|---|---|---|
| 4,276,882 A | 7/1981 | Dickhudt et al. | |
| 4,462,401 A | 7/1984 | Burgio | |
| 4,858,623 A | 8/1989 | Bradshaw et al. | |
| 5,158,097 A | 10/1992 | Christlieb | |
| 5,522,874 A * | 6/1996 | Gates | 607/127 |
| 5,531,781 A * | 7/1996 | Alferness et al. | 607/122 |
| 5,865,843 A | 2/1999 | Baudino | |
| 6,181,969 B1 | 1/2001 | Gord | |

(Continued)

FOREIGN PATENT DOCUMENTS

EP 0085417 8/1983

(Continued)

OTHER PUBLICATIONS

Barclay, L., "Sacral Nerve Stimulation Promising for Fecal Incontinence," Medscape Medical News, downloaded May 14, 2009, www.medscape.com.

(Continued)

*Primary Examiner* — George Manuel
*Assistant Examiner* — Robert N Wieland
(74) *Attorney, Agent, or Firm* — Frommer Lawrence & Haug LLP; Bruce E. Black

(57) ABSTRACT

A nerve stimulation lead has a distal end, a proximal end, and a longitudinal length. The nerve stimulation lead includes a plurality of electrodes disposed at the distal end, a plurality of terminals disposed at the proximal end, and a plurality of conductive wires electrically coupling the plurality of electrodes electrically to the plurality of terminals. The nerve stimulation lead also includes at least one anchoring unit disposed on the nerve stimulation lead. The at least one anchoring unit is configured and arranged for anchoring the nerve stimulation lead against a bony structure.

18 Claims, 16 Drawing Sheets

U.S. PATENT DOCUMENTS

| | | |
|---|---|---|
| 6,192,279 B1 | 2/2001 | Barreras, Sr. et al. |
| 6,360,750 B1 | 3/2002 | Gerber et al. |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 6,792,314 B2 | 9/2004 | Byers et al. |
| 6,847,849 B2 | 1/2005 | Mamo et al. |
| 6,901,287 B2 | 5/2005 | Davis et al. |
| 6,978,180 B2 | 12/2005 | Tadlock |
| 7,069,083 B2 | 6/2006 | Finch et al. |
| 7,072,719 B2 | 7/2006 | Vinup et al. |
| 7,244,150 B1 | 7/2007 | Brase et al. |
| 7,343,202 B2 | 3/2008 | Mrva et al. |
| 7,447,546 B2 | 11/2008 | Kim et al. |
| 7,761,165 B1 | 7/2010 | He et al. |
| 8,019,443 B2 | 9/2011 | Schleicher et al. |
| 2001/0000187 A1 | 4/2001 | Peckham et al. |
| 2003/0078623 A1 | 4/2003 | Weinberg et al. |
| 2003/0114905 A1 | 6/2003 | Kuzma |
| 2003/0208247 A1 | 11/2003 | Spinelli et al. |
| 2004/0116977 A1 | 6/2004 | Finch et al. |
| 2005/0165465 A1 | 7/2005 | Pianca et al. |
| 2005/0283202 A1 | 12/2005 | Gellman |
| 2005/0288760 A1 | 12/2005 | Machado et al. |
| 2006/0127158 A1 | 6/2006 | Olson et al. |
| 2006/0161235 A1 | 7/2006 | King |
| 2006/0206162 A1 | 9/2006 | Wahlstrand et al. |
| 2007/0050005 A1 | 3/2007 | Lauro |
| 2007/0150007 A1 | 6/2007 | Anderson et al. |
| 2007/0150036 A1 | 6/2007 | Anderson et al. |
| 2007/0161294 A1 | 7/2007 | Brase et al. |
| 2007/0219595 A1 | 9/2007 | He |
| 2007/0239243 A1 | 10/2007 | Moffitt et al. |
| 2007/0255367 A1* | 11/2007 | Gerber et al. .................. 607/116 |
| 2007/0255368 A1* | 11/2007 | Bonde et al. .................. 607/116 |
| 2007/0255369 A1 | 11/2007 | Bonde et al. |
| 2007/0255383 A1* | 11/2007 | Gerber et al. .................. 607/149 |
| 2008/0071320 A1 | 3/2008 | Brase |
| 2008/0091255 A1 | 4/2008 | Caparso et al. |
| 2008/0103580 A1* | 5/2008 | Gerber .......................... 607/149 |
| 2008/0140169 A1 | 6/2008 | Imran |
| 2008/0172116 A1 | 7/2008 | Mrva et al. |
| 2008/0183241 A1 | 7/2008 | Bedenbaugh |
| 2008/0183253 A1 | 7/2008 | Bly |
| 2008/0243220 A1 | 10/2008 | Barker |
| 2008/0312712 A1 | 12/2008 | Penner |
| 2009/0012592 A1* | 1/2009 | Buysman et al. ............. 607/116 |

FOREIGN PATENT DOCUMENTS

| | | |
|---|---|---|
| WO | 99/53994 | 10/1999 |
| WO | 00/13743 A1 | 3/2000 |
| WO | 2004/054655 | 7/2004 |
| WO | 2006/086363 A2 | 8/2006 |
| WO | 2007/056384 A2 | 5/2007 |
| WO | 2007/083108 A2 | 7/2007 |
| WO | 2007/149994 A2 | 12/2007 |
| WO | 2008/094789 A1 | 8/2008 |
| WO | 2008/121708 A2 | 10/2008 |

OTHER PUBLICATIONS

Office Communication for U.S. Appl. No. 12/413,081 mailed Feb. 14, 2011.

Office Communication for U.S. Appl. No. 12/413,081 mailed May 16, 2011.

* cited by examiner

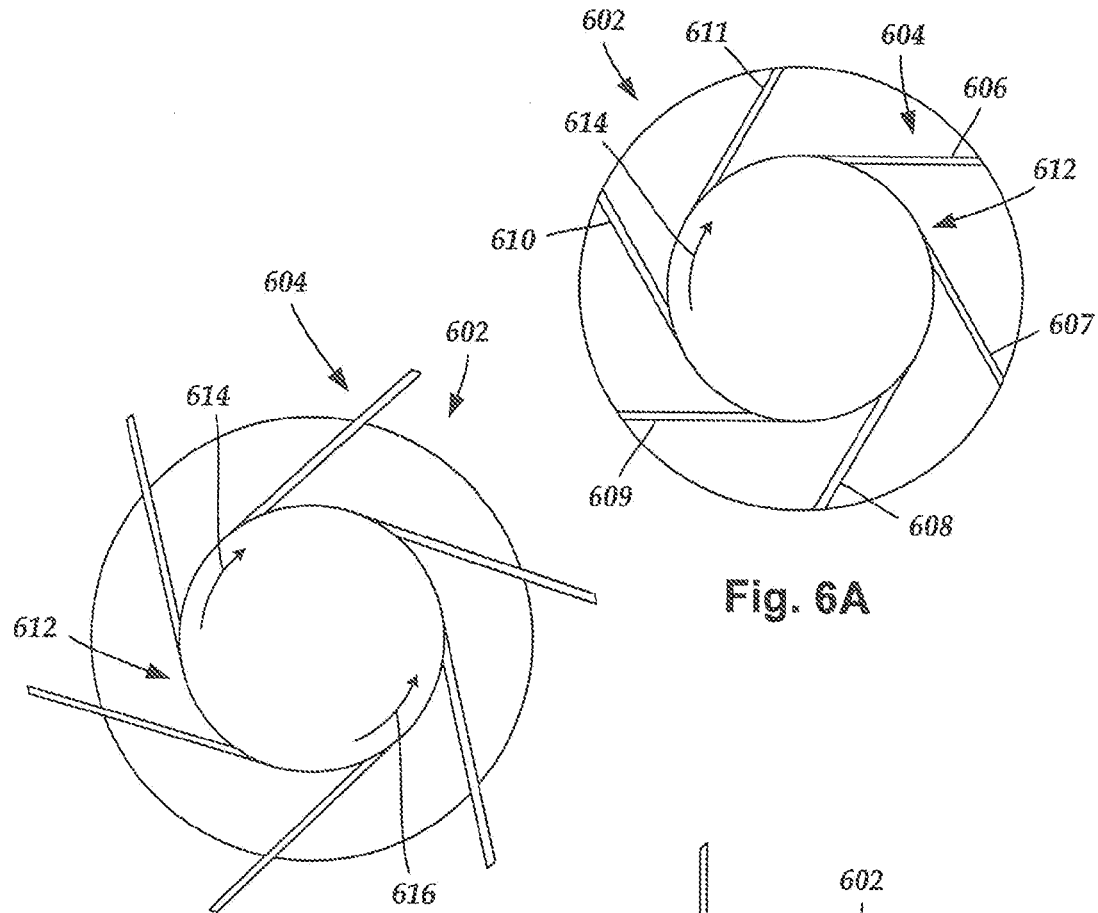
Fig. 6A
Fig. 6B
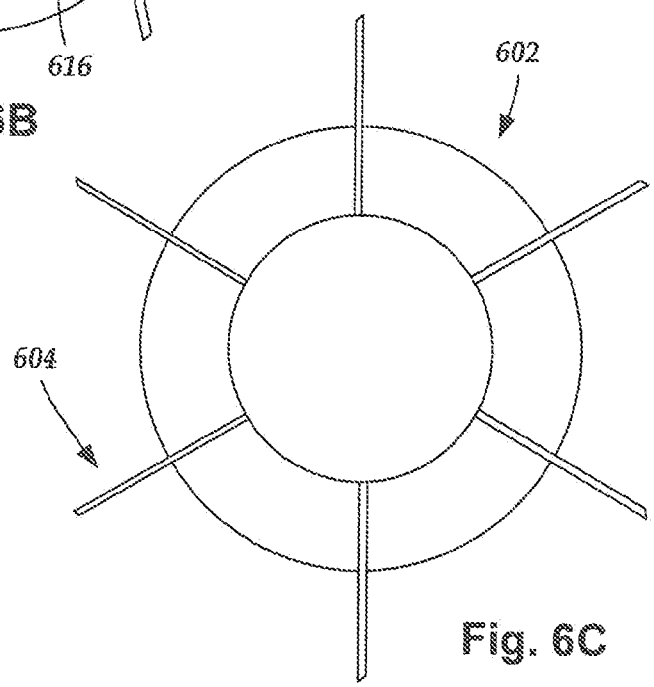
Fig. 6C

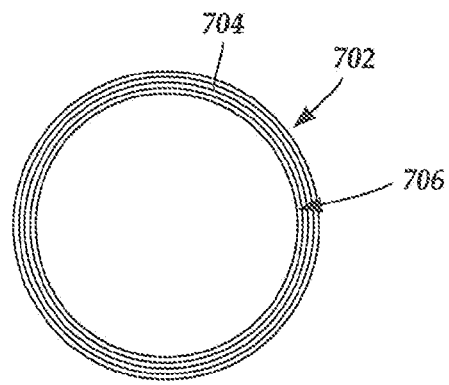
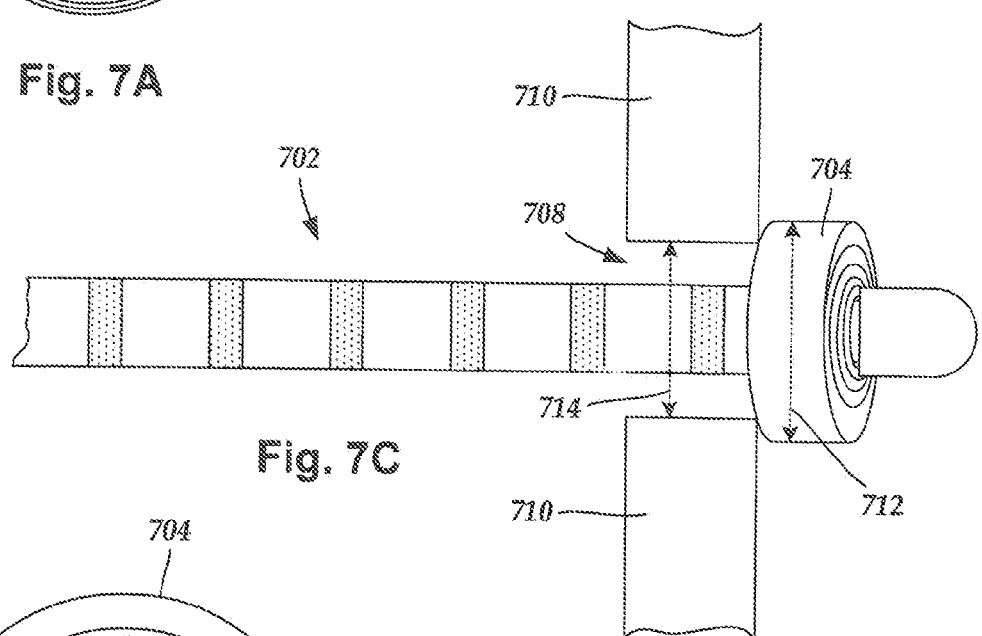
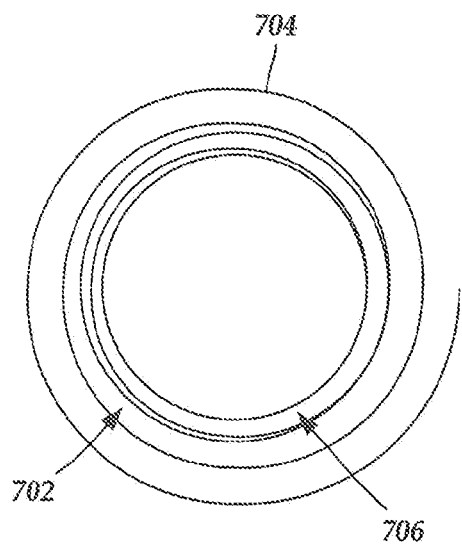

ANCHORING UNITS FOR LEADS OF IMPLANTABLE ELECTRIC STIMULATION SYSTEMS AND METHODS OF MAKING AND USING

CROSS-REFERENCE TO RELATED APPLICATIONS

This patent application is a continuation of U.S. patent application Ser. No. 12/413,081 filed on Mar. 27, 2009, which claimed the benefit of U.S. Provisional Patent Application No. 61/041,536 filed on Apr. 1, 2008, all of which are incorporated herein by reference.

TECHNICAL FIELD

The present invention is directed to the area of implantable electrical stimulation systems and methods of making and using the systems. The present invention is also directed to implantable electrical stimulation systems having leads with one or more anchoring units coupled to the leads for anchoring the leads on or around foramina of bony structures, as well as methods of making and using the anchoring units, leads, and implantable electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Deep brain stimulation has also been useful for treating refractory chronic pain syndromes and has been applied to treat movement disorders and epilepsy. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Moreover, electrical stimulation systems can be implanted subcutaneously to stimulate subcutaneous tissue including subcutaneous nerves such as the occipital nerve.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, a nerve stimulation lead has a distal end, a proximal end, and a longitudinal length. The nerve stimulation lead includes a plurality of electrodes disposed at the distal end, a plurality of terminals disposed at the proximal end, and a plurality of conductive wires electrically coupling the plurality of electrodes electrically to the plurality of terminals. The nerve stimulation lead further includes at least one anchoring unit disposed on the nerve stimulation lead. The at least one anchoring unit is configured and arranged for anchoring the nerve stimulation lead against a bony structure.

In another embodiment, a lead assembly includes a nerve stimulation lead and a spring configured and arranged to anchor the nerve stimulation lead during implantation of the nerve stimulation lead. The nerve stimulation lead has a distal end, a proximal end, and a longitudinal length. The nerve stimulation lead includes a plurality of electrodes disposed at the distal end, a plurality of terminals disposed at the proximal end, and a plurality of conductive wires electrically coupling the plurality of electrodes electrically to the plurality of terminals. The spring is disposed around at least a portion of the nerve stimulation lead.

In yet another embodiment, a nerve stimulation lead has a distal end, a proximal end, and a longitudinal length. The nerve stimulation lead includes a plurality of electrodes disposed at the distal end, a plurality of terminals disposed at the proximal end, and a plurality of conductive wires electrically coupling the plurality of electrodes electrically to the plurality of terminals. The nerve stimulation lead also includes a plurality of tines configured and arranged circumferentially around the nerve stimulation lead. Each tine has an undeployed position in which it lies against the lead and a deployed position in which it projects outward from the lead. The plurality of tines are configured and arranged to change from the undeployed position to the deployed position by rotating at least a portion of the nerve stimulation lead after the nerve stimulation lead has been implanted in a body of a patient.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 6A is a schematic axial cross-sectional view of one embodiment of a lead that includes a plurality of tines spirally arranged in undeployed positions in an annular groove disposed on the lead, according to the invention;

FIG. 6B is a schematic axial cross-sectional view of one embodiment of the lead shown in FIG. 6A with a plurality of tines spirally arranged in partially deployed positions in an annular groove disposed on the lead, according to the invention;

FIG. 6C is a schematic axial cross-sectional view of one embodiment of the lead shown in FIG. 6A with a plurality of tines spirally arranged in fully deployed positions in an annular groove disposed on the lead, according to the invention;

FIG. 7A is a schematic axial cross-sectional view of one embodiment of a lead with a spring disposed in an undeployed position in an annular groove disposed on the lead, according to the invention;

FIG. 7B is a schematic axial cross-sectional view of one embodiment of the lead shown in FIG. 7A with a spring disposed in a deployed position in an annular groove disposed on the lead, according to the invention;

FIG. 7C is a schematic side view of one embodiment of a distal portion of the lead shown in FIG. 7A extending through a foramen of a sacrum and anchored to the sacrum by a spring disposed in a deployed position on the lead distal to a plurality of electrodes, according to the invention;

DETAILED DESCRIPTION

The present invention is directed to the area of implantable electrical stimulation systems and methods of making and using the systems. The present invention is also directed to implantable electrical stimulation systems designed for sacral nerve stimulation, the systems having leads secured on or around sacra by one or more anchoring units coupled to the leads, as well as methods of making and using the anchoring units, leads, and electrical stimulation systems.

Suitable implantable electrical stimulation systems include, but are not limited to, a least one lead with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741,892; and U.S. patent application Ser. Nos. 10/353,101, 10/503,281, 11/238,240; 11/319,291; 11/327,880; 11/375,638; 11/393,991; and 11/396,309, all of which are incorporated by reference.

Figure 1:
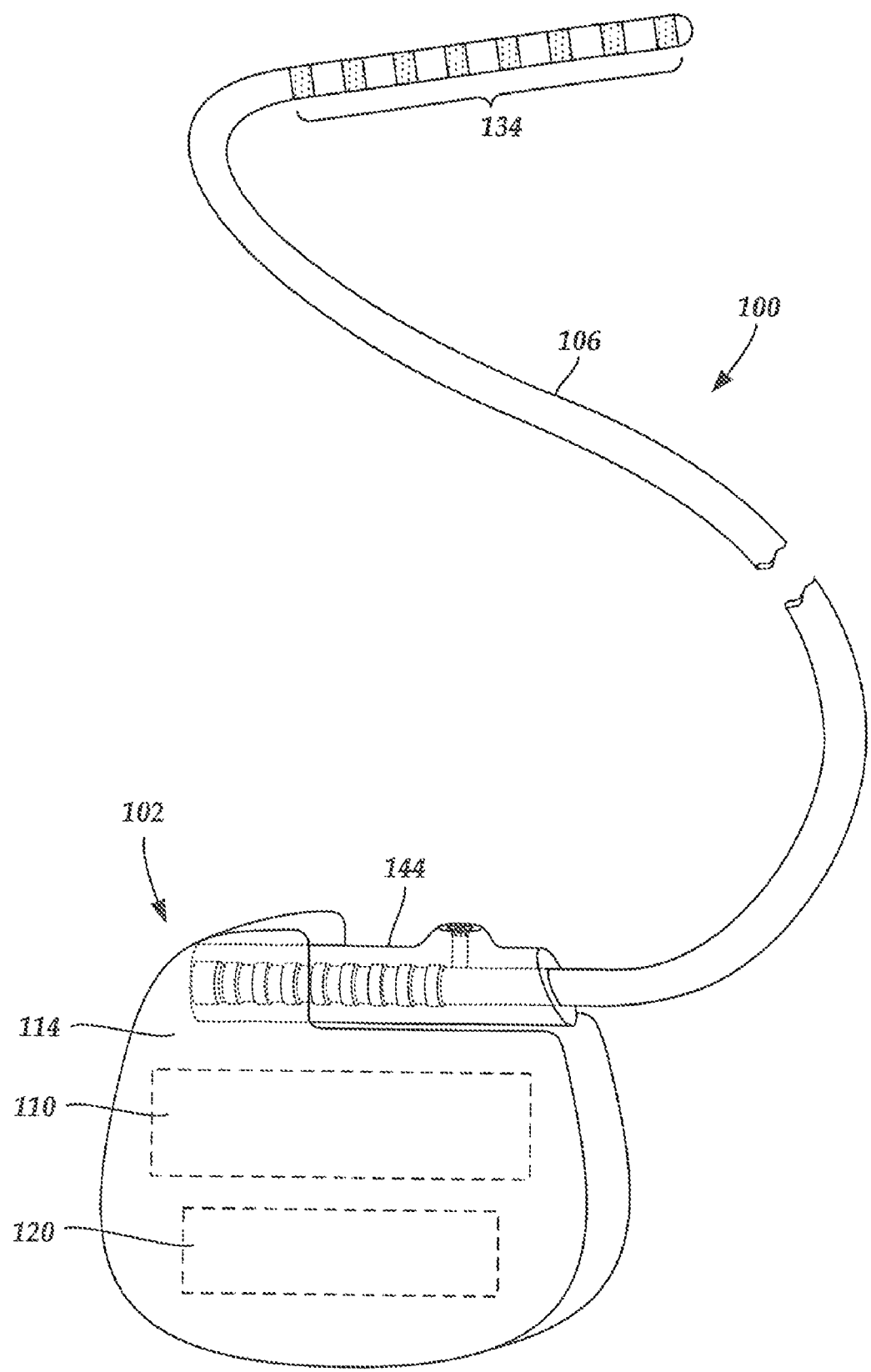
FIG. 1 is a schematic view of one embodiment of an electrical stimulation system, according to the invention.

FIG. 1 illustrates schematically one embodiment of an electrical stimulation system 100. The electrical stimulation system includes a control module (e.g., a stimulator or pulse generator) 102 and at least one lead body 106 ("lead") coupled to the control module 102. Each lead 106 typically includes an array of electrodes 134. The control module 102 typically includes an electronic subassembly 110 and an optional power source 120 disposed in a sealed housing 114. The control module 102 typically includes a connector 144 (FIG. 2A, see also 222 and 250 of FIG. 2B) into which the proximal end of the one or more leads 106 can be plugged to make an electrical connection via conductive contacts on the control module 102 and terminals (e.g., 210 in FIGS. 2A and 236 of FIG. 2B) on each of the one or more leads 106. In at least some embodiments, a lead is isodiametric along a longitudinal length of the lead body 106. In addition, one or more lead extensions 224 (see FIG. 2B) can be disposed between the one or more leads 106 and the control module 102 to extend the distance between the one or more leads 106 and the control module 102 of the embodiment shown in FIG. 1.

The electrical stimulation system or components of the electrical stimulation system, including one or more of the leads 106 and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of one or more leads 106 are typically disposed in, or separated by, a non-conductive, biocompatible material such as, for example, silicone, polyurethane, polyetheretherketone ("PEEK"), epoxy, and the like or combinations thereof. The leads 106 may be formed in the desired shape by any process including, for example, molding (including injection molding), casting, and the like. The non-conductive material typically extends from the distal end of the one or more leads 106 to the proximal end of each of the one or more leads 106.

Terminals (e.g., 210 in FIGS. 2A and 236 of FIG. 2B) are typically disposed at the proximal end of the one or more leads 106 of the electrical stimulation system 100 for connection to corresponding conductive contacts (e.g., 214 in FIGS. 2A and 240 of FIG. 2B) in connectors (e.g., 144 in FIGS. 1-2A and 222 and 250 of FIG. 2B) disposed on, for example, the control module 102 (or to conductive contacts on a lead extension, an operating room cable, or an adaptor). Conductor wires (not shown) extend from the terminals (e.g., 210 in FIGS. 2A and 236 of FIG. 2B) to the electrodes 134. Typically, one or more electrodes 134 are electrically coupled to a terminal (e.g., 210 in FIGS. 2A and 236 of FIG. 2B). In at least some embodiments, each terminal (e.g., 210 in FIGS. 2A and 236 of FIG. 2B) is only connected to one electrode 134. The conductor wires may be embedded in the non-conductive material of the lead 106 or can be disposed in one or more lumens (not shown) extending along the lead 106. In some embodiments, there is an individual lumen for each conductor wire. In other embodiments, two or more conductor wires may extend through a lumen. There may also be one or more lumens (not shown) that open at, or near, the proximal end of the lead 106, for example, for inserting a stylet rod to facilitate placement of the lead 106 within a body of a patient. Additionally, there may also be one or more lumens (not shown) that open at, or near, the distal end of the lead 106, for example, for infusion of drugs or medication into the site of implantation of the one or more leads 106. In at least one embodiment, the one or more lumens may be flushed continually, or on a regular basis, with saline, epidural fluid, or the like. In at least some embodiments, the one or more lumens can be permanently or removably sealable at the distal end.

Figure 2A:
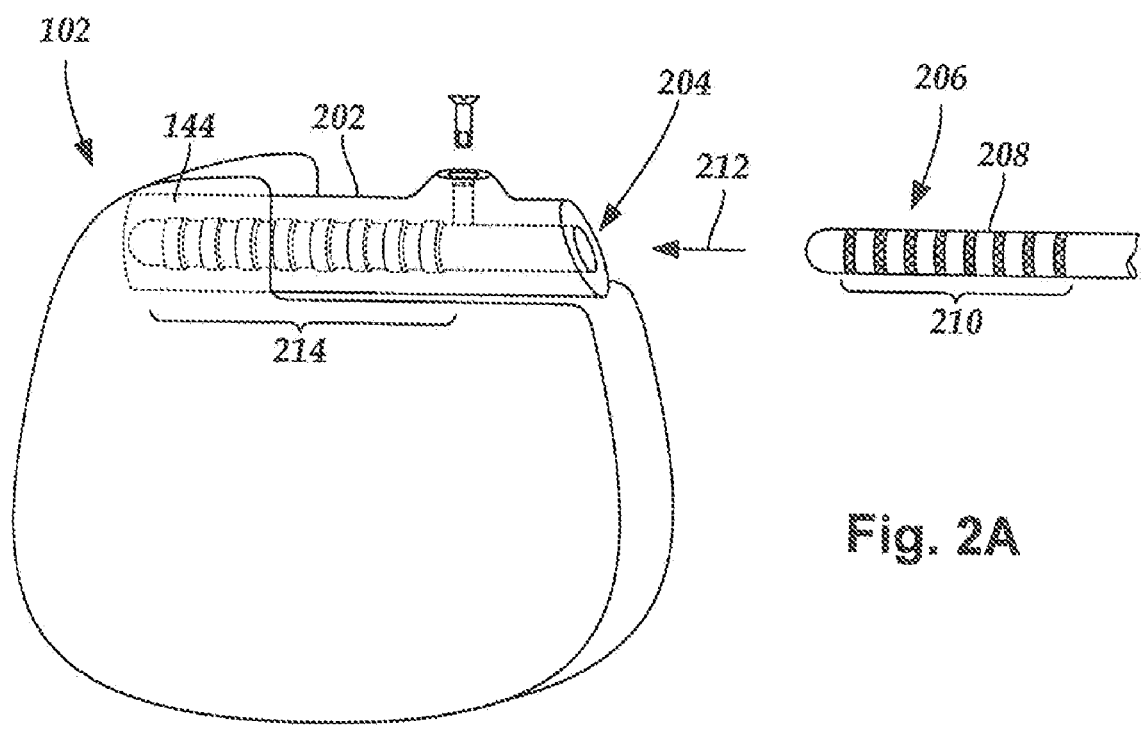
FIG. 2A is a schematic view of one embodiment of a proximal portion of a lead and a control module of an electrical stimulation system, according to the invention.

In at least some embodiments, leads are coupled to connectors disposed on control modules. In FIG. 2A, a lead 208 is shown configured and arranged for insertion to the control module 102. The connector 144 includes a connector housing 202. The connector housing 202 defines at least one port 204 into which a proximal end 206 of a lead 208 with terminals 210 can be inserted, as shown by directional arrow 212. The connector housing 202 also includes a plurality of conductive contacts 214 for each port 204. When the lead 208 is inserted into the port 204, the conductive contacts 214 can be aligned with the terminals 210 on the lead 208 to electrically couple the control module 102 to the electrodes (134 of FIG. 1) disposed at a distal end of the lead 208. Examples of connectors in control modules are found in, for example, U.S. Pat. No. 7,244,150 and U.S. patent application Ser. No. 11/532,844, which are incorporated by reference.

Figure 2B:
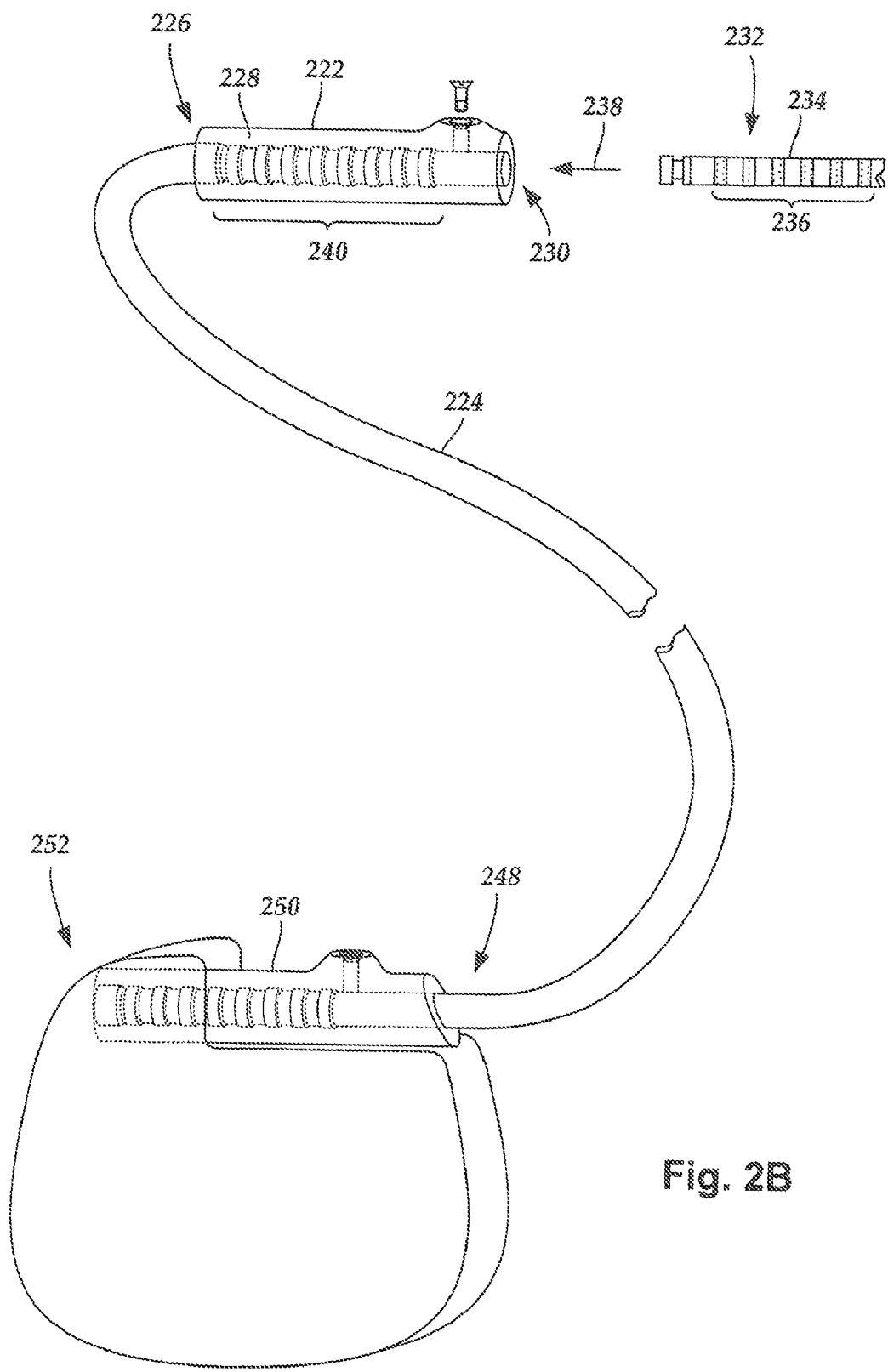
FIG. 2B is a schematic view of one embodiment of a proximal portion of a lead and a lead extension of an electrical stimulation system, according to the invention.

In FIG. 2B, a connector 222 is disposed on a lead extension 224. The connector 222 is shown disposed at a distal end 226 of the lead extension 224. The connector 222 includes a connector housing 228. The connector housing 228 defines at least one port 230 into which a proximal end 232 of a lead 234 with terminals 236 can be inserted, as shown by directional arrow 238. The connector housing 228 also includes a plurality of conductive contacts 240. When the lead 234 is inserted into the port 230, the conductive contacts 240 disposed in the connector housing 228 can be aligned with the terminals 236 on the lead 234 to electrically couple the lead extension 224 to the electrodes (134 of FIG. 1) disposed at a distal end (not shown) of the lead 234.

In at least some embodiments, the proximal end of a lead extension is similarly configured and arranged as a proximal end of a lead. The lead extension 224 may include a plurality of conductive wires (not shown) that electrically couple the conductive contacts 240 to a proximal end 248 of the lead extension 224 that is opposite to the distal end 226. In at least some embodiments, the conductive wires disposed in the lead extension 224 can be electrically coupled to a plurality of terminals (not shown) disposed on the proximal end 248 of the lead extension 224. In at least some embodiments, the proximal end 248 of the lead extension 224 is configured and arranged for insertion into a connector disposed in another lead extension. In other embodiments, the proximal end 248 of the lead extension 224 is configured and arranged for insertion into a connector disposed in a control module. As an example, in FIG. 2B the proximal end 248 of the lead extension 224 is inserted into a connector 250 disposed in a control module 252.

Sometimes leads are used to stimulate nerves that extend through foramina of bony structures, such as sacra. Sacral nerve stimulation is sometimes used for treating one or more different types of ailments, including fecal incontinence, urge incontinence, interstitial cystitis, chronic pelvic pain, and urine retention. Sacral nerves can extend through one or more foramen of a sacrum.

Figure 3:
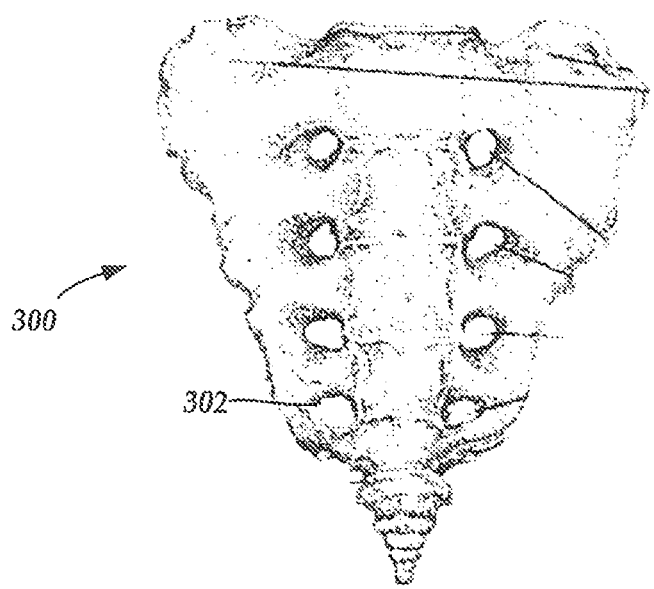
FIG. 3 is a schematic front view of one embodiment of a sacrum that includes foramina through which sacral nerves may extend, according to the invention.

Implantable electrical stimulation systems can sometimes be used for nerve stimulation and tissue stimulation, in general, including, for example, sacral nerve stimulation. One way an electrical stimulation system can be implanted for sacral nerve stimulation is to position a distal end of a lead in or around one or more sacral foramina through which a desired sacral nerve extends. FIG. 3 is a schematic front view of one embodiment of a sacrum 300. The sacrum 300 includes a plurality of foramina, such as foramen 302. Anchoring leads on or around a bony structure, such as sacrum 300, may be difficult due to patient movement occasionally causing anchored leads to dislodge. Previously, some leads have been used that incorporate one or more tines disposed on a lead proximal to the plurality of electrodes. However, such tines may not provide adequate anchoring ability and may not allow a lead to be optimally positioned for stimulation. Additionally, when a distal end of a lead extends through a foramen, one or more proximally-disposed tines may not prevent the migration of the distal end of the lead back through the foramen.

In at least some embodiments, anchoring units are described for use with implantable electrical stimulation systems. In at least some embodiments, the anchoring units are configured and arranged for anchoring on or around foramina of bony structures. For example, in some embodiments, the anchoring units may be used to anchor leads to sacra for use during sacral nerve stimulation. In some embodiments, anchoring units are configured and arranged for anchoring a lead to the walls of a foramen of a bony structure through which the lead extends. In other embodiments, anchoring units are configured and arranged for anchoring a lead to a bony structure by extending the lead through a foramen of the bony structure and anchoring the far side of the bony structure around the foramen to prevent the lead from migrating backwards through the foramen. In alternate embodiments, the anchoring units can also anchor to other features on bony structures, such as grooves, fissures, cracks, and indentations. It will also be understood that these anchoring techniques can also be used to anchor a lead to soft tissue. For example, these anchoring techniques can also be used to anchor a lead to soft tissue on either side of a foramen, or in another location that is not in proximity to a foramen.

Figure 4A:
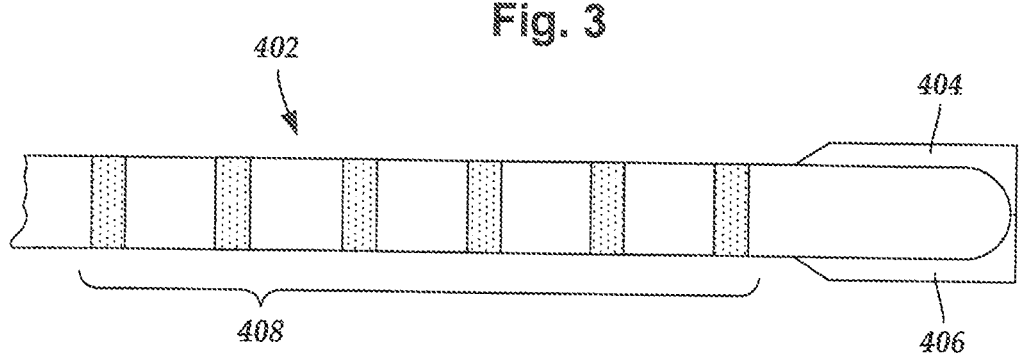
FIG. 4A is a schematic side view of one embodiment of a distal portion of a lead with tines disposed in an undeployed position on the lead distal to a plurality of electrodes, according to the invention.

In some embodiments, an anchoring unit includes one or more tines disposed on a lead distal to a plurality of electrodes, and preferably at a distal tip of the lead. FIG. 4A is a schematic side view of one embodiment of a distal portion of a lead 402 with tines 404 and 406 disposed in undeployed positions on the lead 402 distal to a plurality of electrodes 408. In at least some embodiments, the tines 404 and 406 are generally pressed into or against a longitudinal length of the lead 402 when in an undeployed position, for example in a lead introducer, to facilitate movement of the lead 402 without the tines 404 and 406 catching on anatomical features during implantation. In some embodiments, the tines 404 and 406 overlap each other while in an undeployed position.

The tines 404 and 406 can be formed using any durable, biocompatible material. Examples of suitable materials include metals, alloys, polymers, carbon, and the like, as well as combinations thereof. Any suitable number of tines 404 and 406 may be disposed on the lead 402. For example, one, two, three, four, five, six, or more tines 404 and 406 may be disposed on the lead 402. As will be recognized, other numbers of tines 404 and 406 may also be used.

Figure 4B:
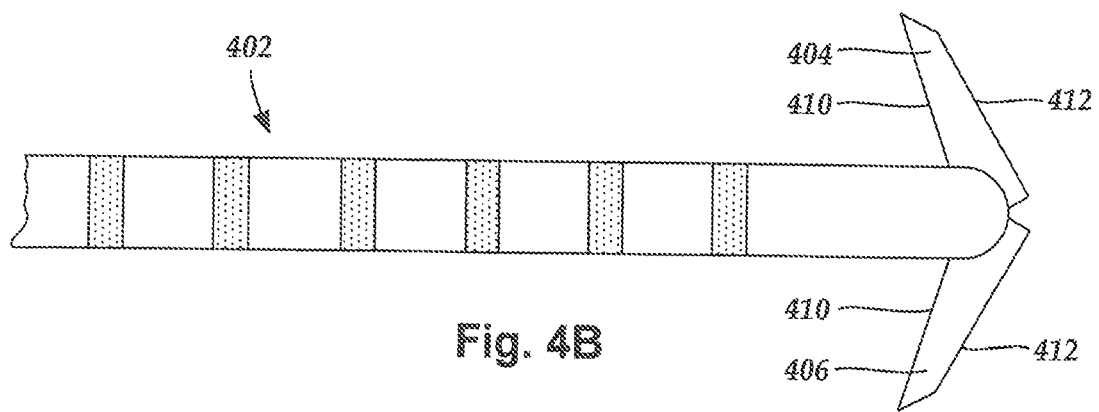
FIG. 4B is a schematic side view of one embodiment of a distal portion of the lead shown in FIG. 4A with tines disposed in a deployed position on the lead distal to a plurality of electrodes, according to the invention.

In at least some embodiments, the tines 404 and 406 can be pivoted into a deployed position. FIG. 4B is a schematic side view of one embodiment of the distal portion of the lead 402 with the tines 404 and 406 disposed in deployed positions on the lead 402 distal to the plurality of electrodes 408. The tines 404 and 406 each include a contact edge 410 and a non-contact edge 412. The shapes of the tines 404 and 406 disposed on the lead 402 may vary. For example, the contact edges 410 of one or more of the tines 404 and 406 may be straight, or curved, or convex, or concave. Similarly, the non-contact edges 412 of one of more of the tines 404 and 406 may be straight, or curved, or convex, or concave. In at least some embodiments, the contact edges 410 of one or more of the tines 404 and 406 may also include one or more jagged regions. For example, teeth may be used to increase the gripping ability of one or more of the tines 404 and 406.

In some embodiments, the tines 404 and 406 are configured and arranged to pivot from an undeployed position to a deployed position by a deployment mechanism (not shown) extending along at least a portion of the longitudinal length of a lead, such as a pullable string, wire, or stylet coupled to the tines 404 and 406 to pivot the tines 404 and 406 from an undeployed position to a deployed position. In at least some embodiments, an adjustment mechanism (not shown), such as a string, wire, or stylet coupled to the tines 404 and 406 can be used to adjust the angle or the positions of the tines 404 and 406, either together or individually, to improve the anchoring ability of the lead 402.

In some embodiments, the tines 404 and 406 can pivot back and forth between deployed and undeployed positions. In other embodiments, the tines 404 and 406 can only pivot from an undeployed position to a deployed position. For example, in some embodiments the tines 404 and 406 employ a spring mechanism, or the tines may be made of a resilient material, which deploys when a lead introducer is retracted to pivot to a deployed position and favor maintaining the deployed position. In which case, a sleeve, such as a lead introducer, can be used to facilitate implantation of the lead 402. Once the lead 402 is positioned, re-positioning or subsequent explantation of the lead 402 may be facilitated by incorporation of the tines 404 and 406 that can pivot back and forth between deployed and undeployed positions.

Figure 4C:
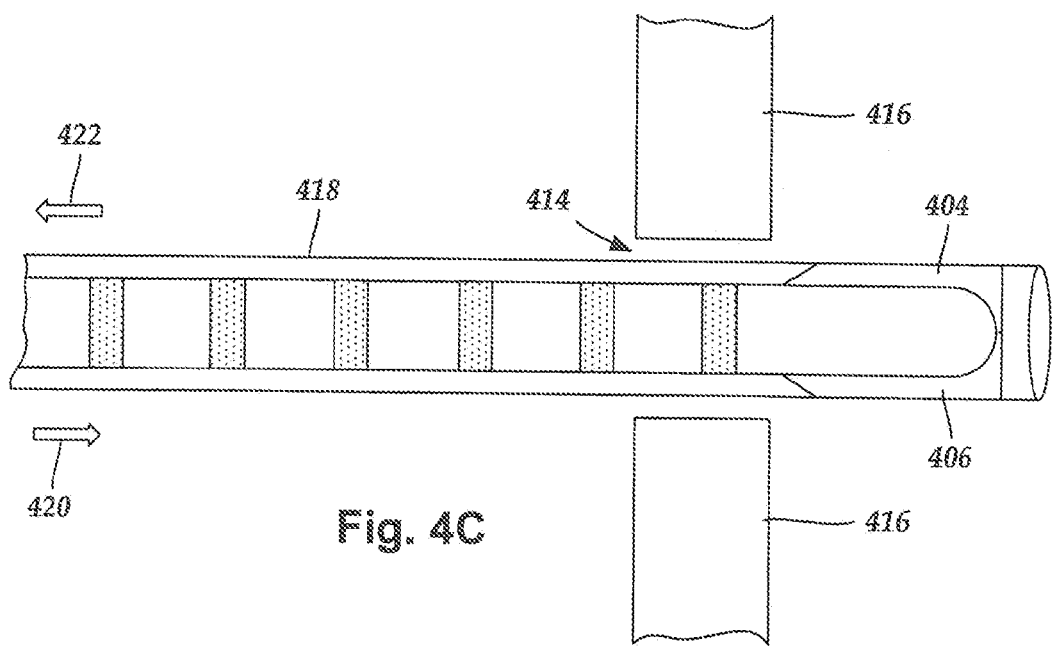
FIG. 4C is schematic side view of one embodiment of a distal portion of the lead shown in FIG. 4A extending through a foramen of a sacrum, the lead having tines disposed on the lead distal to a plurality of electrodes, the lead also having a portion of a sleeve disposed over the tines to maintain the tines in an undeployed position, according to the invention.

FIG. 4C is schematic side view of one embodiment of a distal portion of the lead 402 extending through a foramen 414 of a bony structure 416. The lead 402 includes the tines 404 and 406 disposed in undeployed positions. A lead introducer 418 is disposed over at least a portion of the tines 404 and 406. In at least some embodiments, the lead introducer 418 can be used during implantation of the lead 402 to maintain the tines 404 and 406 in an undeployed position. In at least some embodiments, the distal portion of the lead 402 and the lead introducer 418 are implanted by extending the distal portion of the lead 402 and the lead introducer 418 through the foramen 414 of the sacrum 416 in a direction shown by directional arrow 420. In at least some embodiments, once the distal end of the lead 402 extends through the foramen 414, the lead introducer 418 can be removed from the lead 402 in a direction shown by directional arrow 422.

Figure 4D:
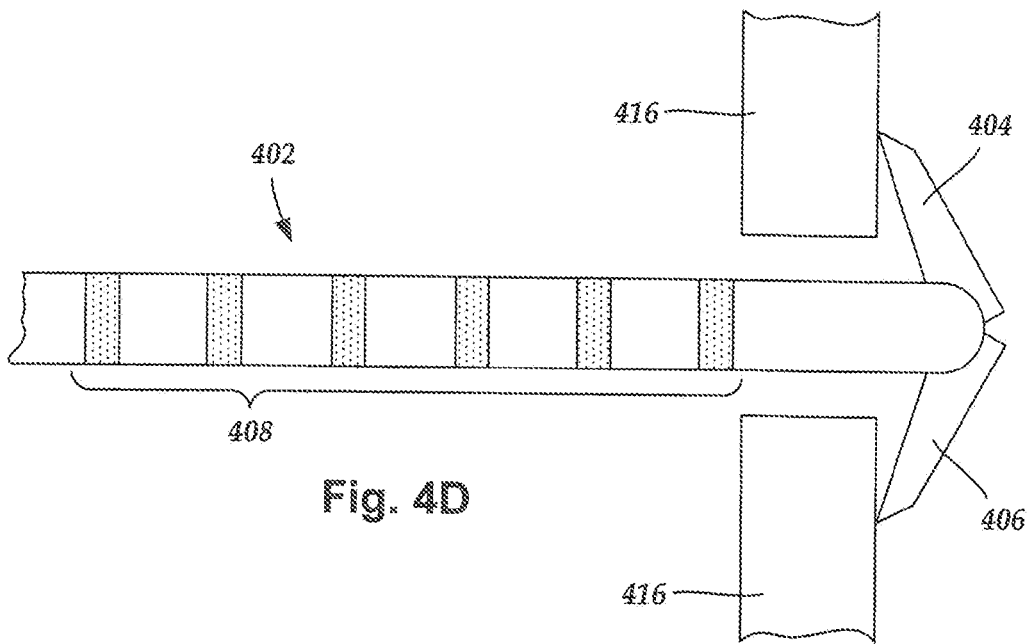
FIG. 4D is a schematic side view of one embodiment of a distal portion of the lead shown in FIG. 4C extending through a foramen of a sacrum and anchored to the sacrum by tines disposed in deployed positions at the distal portion of the lead, according to the invention.

In at least some embodiments, once a distal end of the lead 402 is passed through the foramen 414 and the tines 404 and 406 are pivoted from an undeployed position to a deployed position, the tines 404 and 406 may be used to anchor the lead 402 against the bony structure 416 surrounding the foramen 414. FIG. 4D is a schematic side view of one embodiment of the distal portion of the lead 402 anchored to the bony structure 416 by the tines 404 and 406 disposed in deployed positions on the lead 402 distal to the plurality of electrodes 408. It will be understood that the tines 404 and 406 may also be used to anchor leads in other parts of a body, including anchoring the lead 402 against bone, cartilage, and even anchoring in soft tissue. It will be understood that the tines 404 and 408 may be disposed on the lead 402 proximal to the plurality of electrodes 408 or between adjacent electrodes of the plurality of electrodes 408 in addition to, or instead of, distal to the plurality of electrodes 408.

Figure 5A:
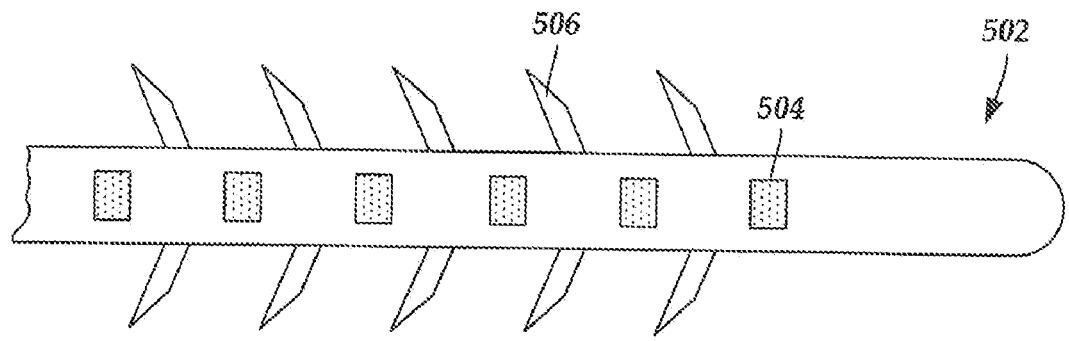
FIG. 5A is a schematic side view of one embodiment of a distal portion of a lead with tines in deployed positions disposed between each of a plurality of electrodes, according to the invention.

In some embodiments, an anchoring unit includes one or more tines disposed on a lead between adjacent electrodes. FIG. 5A is a schematic side view of one embodiment of a distal portion of a lead 502. The lead 502 includes a plurality of electrodes, such as electrode 504, and a plurality of tines, such as tine 506, disposed in deployed positions between adjacent electrodes. In FIG. 5A, two tines are shown disposed between adjacent electrodes. However, any number of tines can be disposed between adjacent electrodes. For example, there can be one, two, three, four, five, six, seven, eight, nine, ten, or more tines disposed between adjacent electrodes. As will be recognized, other numbers of tines may also be disposed between adjacent electrodes. In some embodiments, one or more rings of tines may be disposed between adjacent electrodes. Each ring of tines may include any number of tines.

Figure 5B:
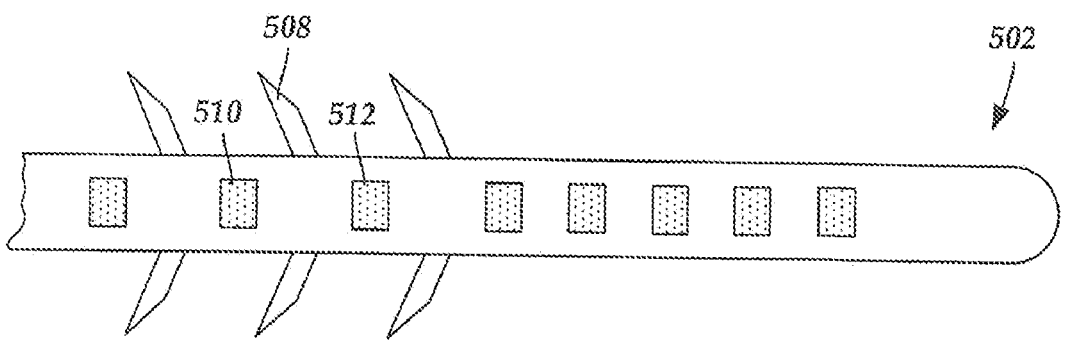
FIG. 5B is a schematic side view of one embodiment of a distal portion of the lead shown in FIG. 5A with tines in deployed positions disposed between some of a plurality of electrodes, according to the invention.

In alternate embodiments, the tines are disposed between some adjacent electrodes and are not disposed between other adjacent electrodes. FIG. 5B is a schematic side view of the lead 502 with a tine, such as tine 508, disposed between some adjacent electrodes, such as adjacent electrodes 510 and 512. In at least some embodiments, the tines shown in FIGS. 5A and 5B can be pivoted between undeployed positions and deployed positions and adjusted in a similar manner as the tines shown in FIGS. 4A and 4B. Additionally, in some embodiments, the tines shown in FIGS. 5A and 5B can overlap one another while undeployed.

Figure 5C:
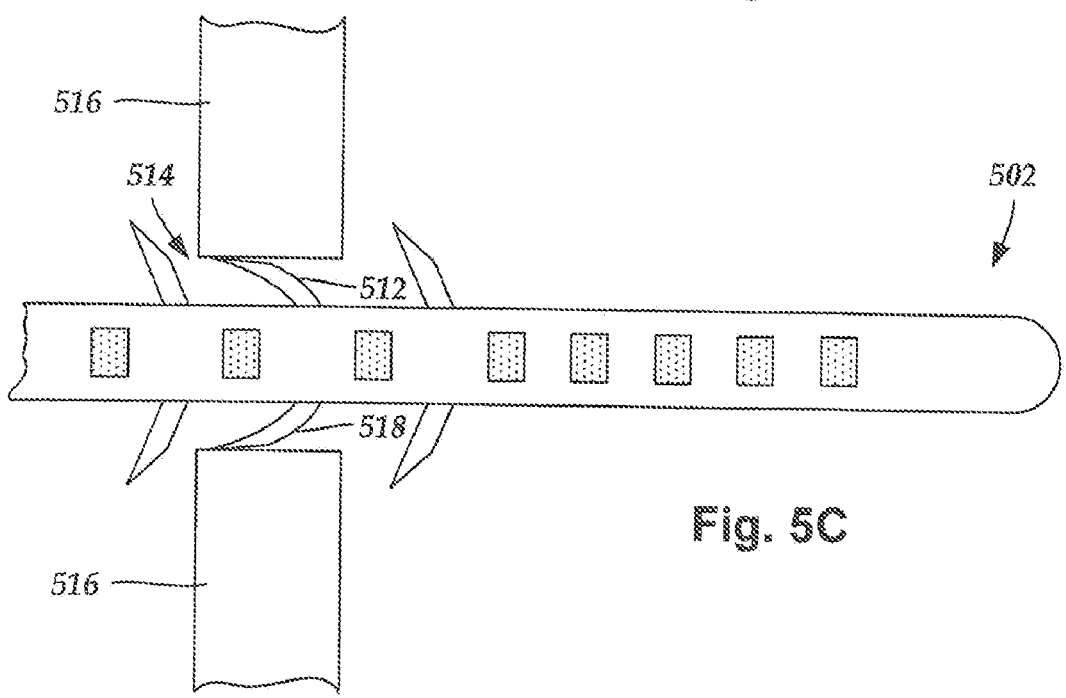
FIG. 5C is a schematic side view of one embodiment of a distal portion of the lead shown in FIG. 5B anchored to the walls of a foramen of a sacrum by tines disposed in deployed positions between some electrodes at the distal portion of the lead, according to the invention.

FIG. 5C is a schematic side view of one embodiment of the distal portion of the lead 502 extending through a foramen 514 of a bony structure 516. The lead 502 is anchored to the walls of the foramen 514 by tines disposed in deployed positions between some adjacent electrodes at the distal portion of the lead 502. In some embodiments, the tines shown in FIGS. 5A and 5B are formed from materials with suitable flexibility to facilitate anchoring within the foramen 514 without damaging nerves and other vessels within the foramen 514. In FIG. 5C, tines 512 and 518 are shown bent against the walls of the foramen 514. It will be understood that the tines may be disposed on the lead 502 proximal to or distal to the plurality electrodes in addition to, or instead of, between adjacent electrodes. Once the lead 502 is positioned, re-positioning or subsequent explantation of the lead 502 may be facilitated by incorporation of the tines that can pivot back and forth between deployed and undeployed positions.

In some embodiments, an anchoring unit disposed on a lead includes one or more tines that are arranged spirally around the circumference of a lead when in an undeployed position. FIG. 6A is a schematic axial cross-sectional view of one embodiment of a lead 602 that includes a plurality of tines 604, such as tines 606-611, disposed spirally in undeployed positions in an annular groove 612 disposed on the lead 602. The tines 604 can have any suitable shape for anchoring. For example, the tines 604 may have shapes that are rod-shaped, plate-shaped, wing-shaped, branch-shaped, and the like. As will be recognized, other shapes may also be used. Additionally, the cross-sectional shapes of the tines 604 may have any suitable form. For example, the tines 604 may have cross-sectional shapes that are round, triangular, rectangular, semi-circular, and the like. As will be recognized, other cross-sectional shapes may also be used. In some embodiments, the tines have at least one sharp edge configured and arranged for anchoring to bone. In other embodiments, the tines have at least one blunt end configured and arranged for anchoring to soft tissue or to ameliorate damage to tissue and vessels when anchoring to bone.

In at least some embodiments, the tines 604 are transitioned to deployed positions by twisting or rotating a first portion of the lead 602 in relation to a second portion of the lead 602. For example, in at least some embodiments, twisting or rotating a portion of the lead 602 in a clockwise direction, as shown by directional arrow 614, causes the tines 604 to advance from the annular groove 612. In at least some embodiments, the rate of deployment of the tines 604 may be controlled by the twisting or rotation rate. In at least some embodiments, the amount of twisting or rotating of the first portion of the lead 602 in relation to the second portion of the lead 602 controls the amount of the tines 604 advanced from the annular groove 612. In at least some embodiments, the amount of twisting or rotating of the first portion of the lead 602 in relation to the second portion of the lead 602 controls the angle the times 604 form with the lead 602 in addition to, or instead of, the amount of the tines 604 advanced from the annular groove 612.

FIG. 6B is a schematic axial cross-sectional view of one embodiment of the tines 604 in partially-deployed positions. In at least some embodiments, counterclockwise twisting or rotating, as shown by directional arrow 616, of the first portion of the lead 602 in relation to the second portion of the lead 602, causes the tines 604 to retract towards undeployed positions, as shown in FIG. 6A. In other embodiments, deploying the tines 604 is substantially permanent and the tines 604 are not returned to their undeployed position by twisting or rotating in the opposite direction. For example, the deployment of the tines 604 may release tine stops, or move the tines 604 past tine stops, thereby preventing return of the tines to an undeployed position.

In at least some embodiments, additional clockwise twisting or rotating 614 of the first portion of the lead 602 in relation to the second portion of the lead 602 further advances the tines 604 from the annular groove 612. FIG. 6C is a schematic axial cross-sectional view of one embodiment of the tines 604 in fully-deployed positions on the lead 602. In at least some embodiments, a mechanism can be employed to retain the tines 604 in fully-deployed positions. In some embodiments, the retention mechanism for retaining the tines 604 in fully-deployed positions can also be used to retract the tines 604. Once the tines 604 are in either partially deployed positions or fully-deployed positions, the lead 602 can be anchored to a bony structure or to soft tissue, such as soft tissue in proximity to a bony structure. For example, the lead 602 can be anchored to a foramen or to a sacrum on the opposite side of the foramen from the proximal end (not shown) of the lead 602, as shown in FIGS. 5D and 4C, respectively.

Figure 6D:
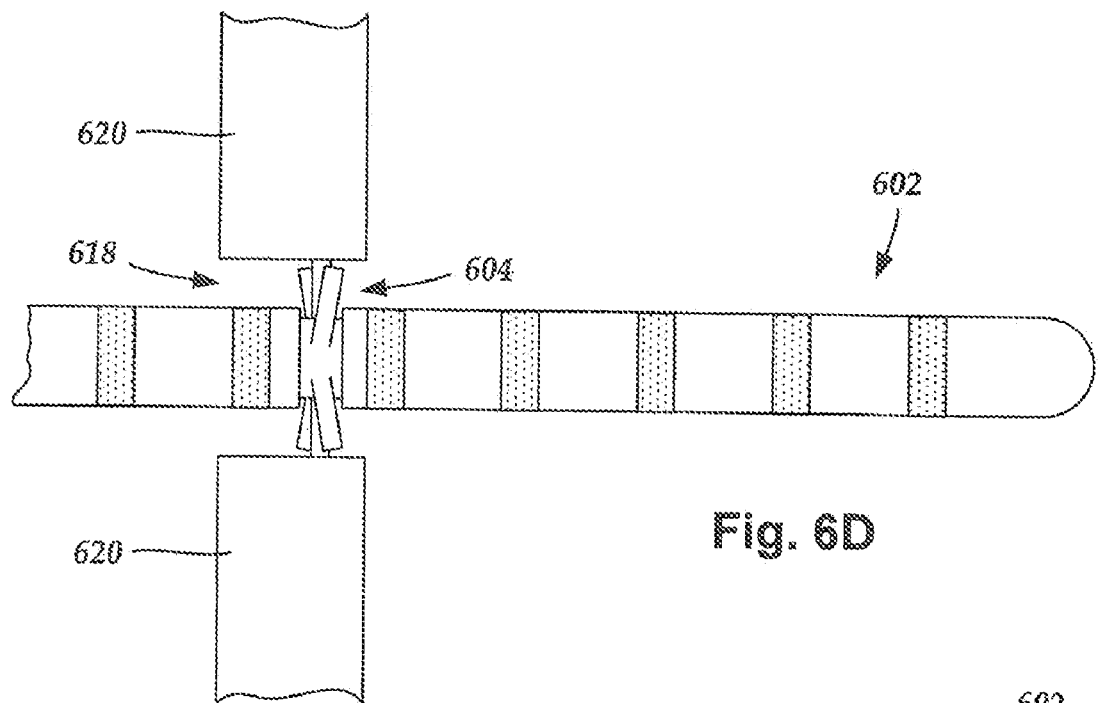
FIG. 6D is a schematic side view of one embodiment of a distal portion of the lead shown in FIG. 6A anchored to the walls of a foramen of a sacrum by a plurality of tines spirally arranged in fully deployed positions in an annular groove disposed at the distal portion of the lead between two electrodes, according to the invention.

FIG. 6D is a schematic side view of one embodiment of the distal portion of the lead 602 extending through a foramen 618 of a sacrum 620 and anchored to the walls of the foramen 618 by the tines 604 in fully-deployed positions at the distal portion of the lead 602. In other embodiments, the tines 604 are disposed in other locations along the longitudinal length of the lead 602. For example, the tines 604 may be disposed distal to the electrodes, or disposed proximal to the electrodes. In at least some embodiments, more than one plurality of tines 604 is disposed on the lead 602. For example, multiple rings of tines 604 may be positioned along the length of the lead 602.

Figure 6E:
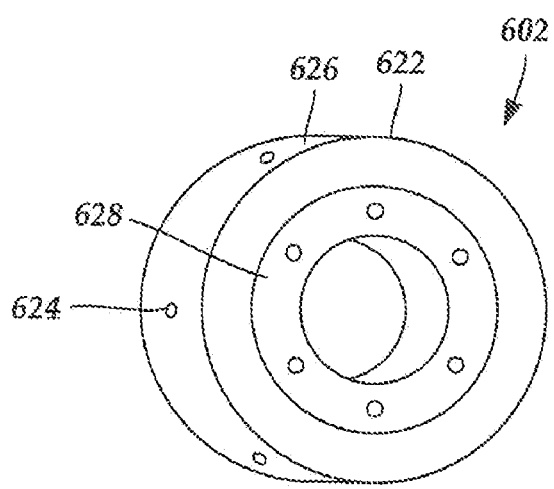
FIG. 6E is a schematic perspective view of one embodiment of a portion of the lead shown in FIG. 6A, the lead including cutouts disposed in an outer ring, according to the invention.
Figure 6F:
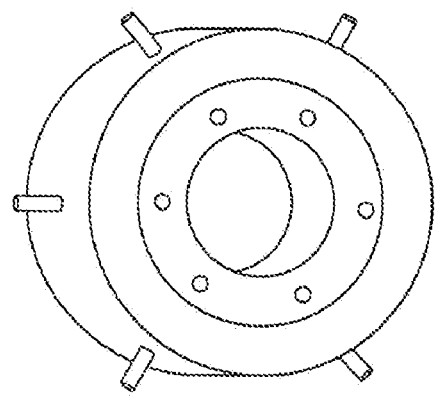
FIG. 6F is a schematic perspective view of one embodiment of a portion of the lead shown in FIG. 6A, the lead including a tine partially advanced from each of a plurality of cutouts disposed in an outer ring, according to the invention.

In at least some embodiments, the tines 604 are disposed in an outer ring of the lead 602 with cutouts for the tines 604. FIG. 6E is a schematic perspective view of one embodiment of a portion of the lead 602 including an outer ring 622 with cutouts, such as cutout 624. In at least some embodiments, the cutouts may be designed such that when a user rotates the outer ring 622 in a first direction, one or more tines 604 advance from each cutout (as shown in FIG. 6F). In at least some embodiments, rotation of the outer ring 622 in a second direction causes the one or more tines 604 to retract. In at least some embodiments, an outer surface 626 of the outer ring 622 is isodiametric with an outer surface of the lead 602. In at least some embodiments, the tines 604 are disposed in an inner ring 628 when in an undeployed position. In alternate embodiments, the tines 604 may be advanced or retracted by rotating the inner ring 628 instead of, or in addition to, rotating the outer ring 622.

In some embodiments, an anchoring unit disposed on a lead includes one or more radially expanding springs. FIG. 7A is a schematic axial cross-sectional view of one embodiment of a lead 702 that includes a spring 704 in an undeployed position disposed in an annular groove 706 on the lead 702. In at least some embodiments, the diameter of the spring 704 while in an undeployed position is no greater than the diameter of the lead 702. FIG. 7B is a schematic axial cross-sectional view of one embodiment of the spring 704 disposed in a deployed position in the annular groove 706 on the lead 702. In at least some embodiments, the diameter of the spring 704 while in a deployed position is greater than the diameter of a lead. In at least some embodiments, the diameter of the spring 704 in a deployed position may be greater than the diameter of the foramen.

In some embodiments, the spring 704 can be implanted using a removable lead introducer disposed over at least a portion of the spring 704 to keep the spring 704 in an undeployed position during positioning of the lead 702 in a similar manner as the lead 402 shown in FIG. 4C. Once the lead 702 is positioned, the introducer may be removed, allowing the spring 704 to use stored potential energy to transfer to a deployed position and anchor the lead 702. In other embodiments, the spring 704 is configured and arranged to remain in an undeployed position by a mechanism that does not include a lead introducer disposed over the spring 704. In some embodiments, the spring 704 may be placed in a deployed position by twisting or rotating a first portion of the lead 702 in relation to a second portion of the lead 702 in a manner similar to the technique described above for the spirally-arranged tines 604. For example, in at least some embodiments, twisting or rotating a portion of the lead 702 in a clockwise direction causes the spring 704 to advance from the annular groove 706 and into a deployed position.

In at least some embodiments, the rate of deployment of the spring 704 may be controlled by the twisting or rotation rate. In at least some embodiments, the amount of twisting or rotating of the first portion of the lead 702 in relation to the second portion of the lead 702 controls the amount of the spring 704 advanced from the annular groove 706. In at least some embodiments, counterclockwise twisting or rotating of the first portion of the lead in relation to the second portion of the lead causes the spring 704 to retract towards an undeployed position, as shown in FIG. 7A. In at least some embodiments, the lead 702 includes a release switch or button for deploying at least a portion of the spring 704 at a predetermined rate using potential energy stored in the spring 704.

In at least some embodiments, the spring 704 can be used to anchor the lead 702 to a bony structure or to soft tissue. FIG. 7C is a schematic side view of one embodiment of the distal portion of the lead 702 extending through a foramen 708 of a bony structure 710 and anchored against the bony structure 710 by the spring 704 disposed in a deployed position on the distal portion of the lead 702. In other embodiments, the spring 704 is disposed in other locations along the longitudinal length of the lead 702. For example, the spring 704 may be disposed between two adjacent electrodes, or disposed along the longitudinal length of the spring 704 proximal to the electrodes. In at least some embodiments, more than one spring 704 is disposed on the lead 702.

As shown in FIG. 7C, the lead 702 extends through the foramen 708 defined in the sacrum 710 and the spring 704 is in a deployed position on an opposite side of the sacrum 710 from a proximal end (not shown) of the lead 702. The spring 704 has a diameter, shown in FIG. 7C as a two-headed dotted arrow 712, and the foramen 708 has a diameter, shown in FIG. 7C as a two-headed dotted arrow 714. The diameter 712 of the spring 704 is greater in length than the diameter 714 of the foramen 708. Thus, the spring 704 in a deployed position prevents the lead 702 from migrating back through the foramen 708. In alternate embodiments, the spring 704 is placed in a deployed position within the foramen 708 to anchor the lead 702 to the foramen 708. In yet other embodiments, the spring 704 is placed in a deployed position to anchor the lead 702 against cartilage or soft tissue. In at least some embodiments, the diameter of the spring 704 in a deployed position is greater than the lead 702, but less than the foramen 708. It will be understood that prevention of migration of the lead 702 may also occur when the diameter of the spring 704 in a deployed position is greater than the lead 702, but less than the diameter of the foramen 708. Note that, in some circumstances it may be undesirable for the diameter of the spring 704 in a deployed position to have a diameter that is less than the diameter of the foramen 708 so as to reduce the risk of damaging soft tissue extending through the foramen 708.

Figure 7D:
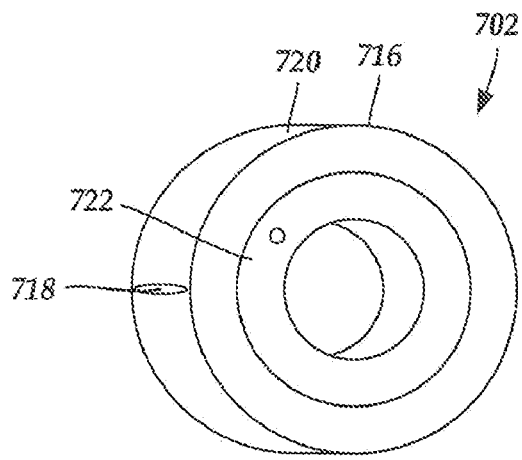
FIG. 7D is a schematic perspective view of one embodiment of a portion of the lead shown in FIG. 7A, the lead including a cutout disposed in an outer ring, according to the invention.
Figure 7E:
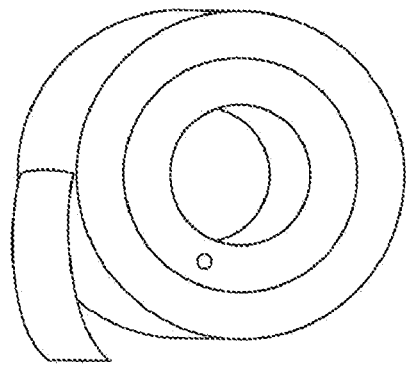
FIG. 7E is a schematic perspective view of one embodiment of a portion of the lead shown in FIG. 7A, the lead including a spring partially advanced from a cutout disposed in an outer ring, according to the invention.

In at least some embodiments, the spring 704 is disposed in an outer ring of the lead 702 with a cutout for the spring 704. FIG. 7D is a schematic perspective view of one embodiment of a portion of the lead 702 including an outer ring 716 with a cutout 718. In at least some embodiments, the cutout 718 may be designed such that when a user rotates the outer ring 716 in a first direction, the spring 704 advances from the cutout 718 (as shown in FIG. 7E). In at least some embodiments, rotation of the outer ring 716 in a second direction causes the spring 704 to retract. In at least some embodiments, an outer surface 720 of the outer ring 716 is isodiametric with an outer surface of the lead 702. In at least some embodiments, the spring 704 is disposed in an inner ring 722 when in an undeployed position. In alternate embodiments, the spring 704 may be advanced or retracted by rotating the inner ring 722 instead of, or in addition to, rotating the outer ring 716.

Figure 8A:
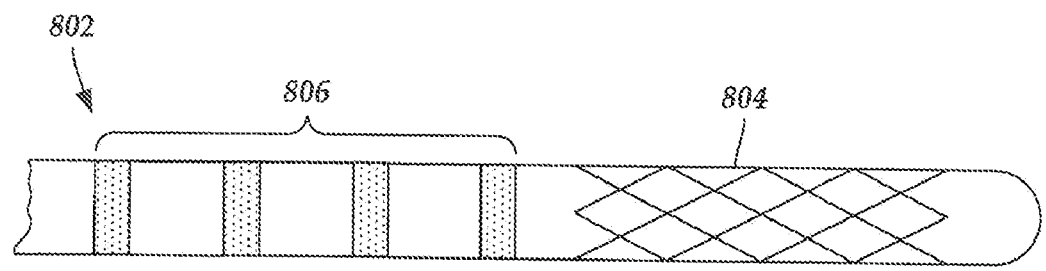
FIG. 8A is a schematic side view of one embodiment of a distal portion of a lead with a stent disposed in an undeployed position over a portion of the lead distal to a plurality of electrodes, according to the invention.

In some embodiments, an anchoring unit disposed on a lead includes one or more expandable stents disposed on a lead. FIG. 8A is a schematic side view of one embodiment of a distal portion of a lead 802 that includes an expandable stent 804 disposed in an undeployed position over a portion of the lead 802 distal to a plurality of electrodes 806. In at least some embodiments, the lead 802 can be positioned while the stent 804 is in an undeployed position. Once the lead 802 is positioned, the stent 804 can be transitioned to a deployed position by expanding the stent 804. In some embodiments, the stent 804 can be implanted using a removable lead introducer disposed over at least a portion of the stent 804 to maintain the stent 804 in an undeployed position during positioning of the lead 702 in a similar manner as the lead 402 shown in FIG. 4C. In alternate embodiments, the stent 804 may also be contractible, so that the stent 804 can transition from a deployed position to an undeployed position.

Figure 8B:
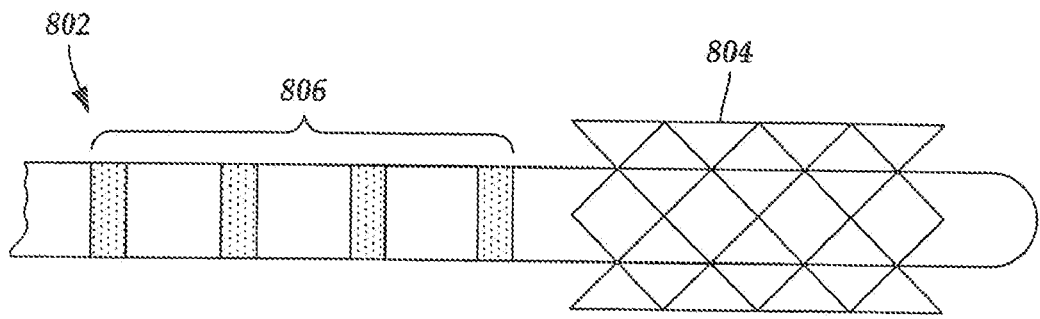
FIG. 8B is a schematic side view of one embodiment of a distal portion of the lead shown in FIG. 8A with a stent disposed in a deployed position over a portion of the lead distal to a plurality of electrodes, according to the invention.

FIG. 8B is a schematic side view of one embodiment of a distal portion of the lead 802. The lead 802 includes the stent 804 disposed in a deployed position over the distal portion of the lead 802. In some embodiments, the stent 804 is positioned between adjacent electrodes 806. In other embodiment, the stent 804 is positioned along a portion of the longitudinal length of the lead 802 proximal to the electrodes 806. In at least some embodiments, more than one stent 804 is disposed on the lead 802.

Figure 8C:
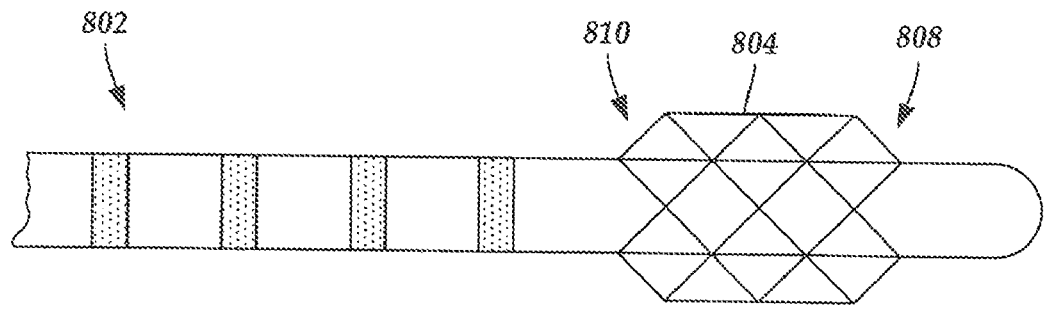
FIG. 8C is a schematic side view of another embodiment of a distal portion of the lead shown in FIG. 8A with a stent disposed in a deployed position over a portion of the lead distal to a plurality of electrodes, according to the invention.

In at least some embodiments, the stent 804 remains coupled to the lead 802 when the stent 804 is in a deployed position. In at least one embodiment, the stent 804 remains coupled to the lead 802 by an attachment mechanism coupled to the stent 804 along an interior surface of the stent 804. In other embodiments, one or more of the ends of the stent 804 remain fixed to the lead 802 when the stent 804 is in a deployed position. FIG. 8C is a schematic side view of another embodiment of a distal portion of the lead 802 including the expandable stent 804 disposed in a deployed position over a portion of the lead 802. The stent 804 includes a distal end 808 and a proximal end 810 that are fixed to the lead 802.

Figure 8D:
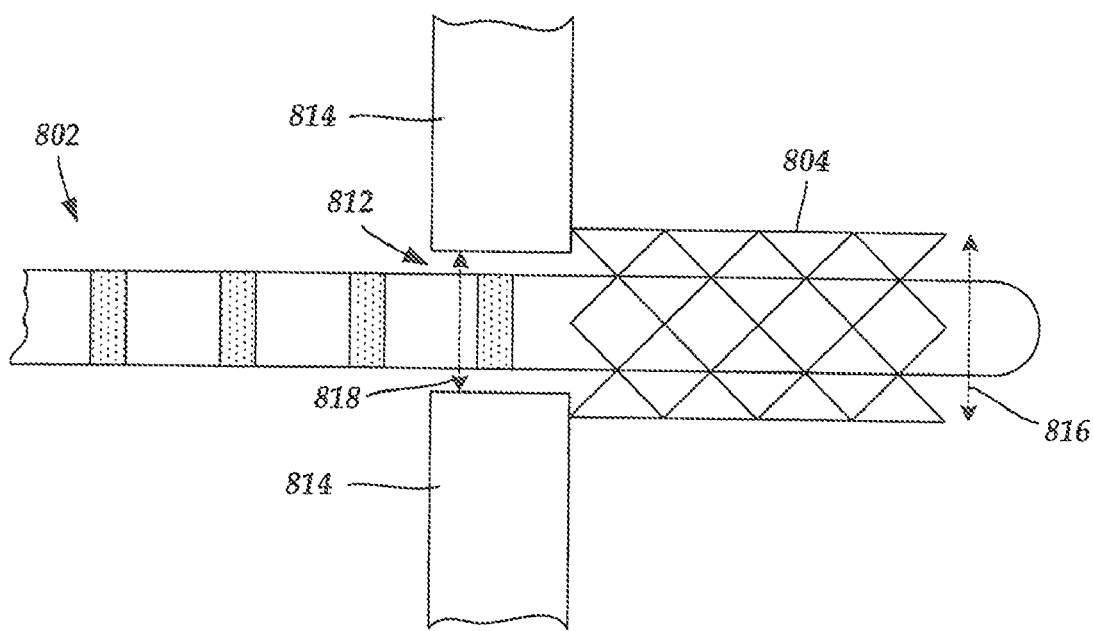
FIG. 8D is a schematic side view of one embodiment of a distal portion of the lead shown in FIG. 8A extending through a foramen of a sacrum and anchored to the sacrum by a stent disposed in a deployed position over a portion of the lead distal to a plurality of electrodes, according to the invention.

In at least some embodiments, the stent 804 can be used to anchor the lead 802 to a bony structure or to soft tissue. FIG. 8D is a schematic side view of one embodiment of the distal portion of the lead 802 extending through a foramen 812 of a bony structure 814 and anchored to the bony structure 814 by the stent 804 disposed in a deployed position on the distal portion of the lead 802. As shown in FIG. 8D, the lead 802 extends through a foramen 812 of the bony structure 814 and the stent 804 is in a deployed position on an opposite side of the sacrum 814 from a proximal end (not shown) of the lead 802. The stent 804 has a diameter, shown in FIG. 8D as a two-headed dotted arrow 816, and the foramen 812 has a diameter, shown in FIG. 8D as a two-headed dotted arrow 818. The diameter 916 of the stent 904 is greater in length than the diameter 818 of the foramen 812. Thus, the stent 804 prevents the lead 802 from migrating back through the foramen 812. In alternate embodiments, the stent 804 is placed in a deployed position within the foramen 812 to anchor the lead 802 to the foramen 812. In yet other embodiments, the stent 804 is placed in a deployed position to anchor the lead 802 against cartilage or soft tissue. In at least some embodiments, the diameter of the stent 804 in a deployed position is greater than the lead 802, but less than the foramen 812. It will be understood that prevention of migration of the lead 802 may also occur when the diameter of the stent 804 in a deployed position is greater than the lead 802, but less than the diameter of the foramen 812. Note that, in some circumstances it may be undesirable for the diameter of the stent 804 in a deployed position to have a diameter that is less than the diameter of the foramen 812 so as to reduce the risk of damaging soft tissue extending through the foramen 812.

Figure 9A:
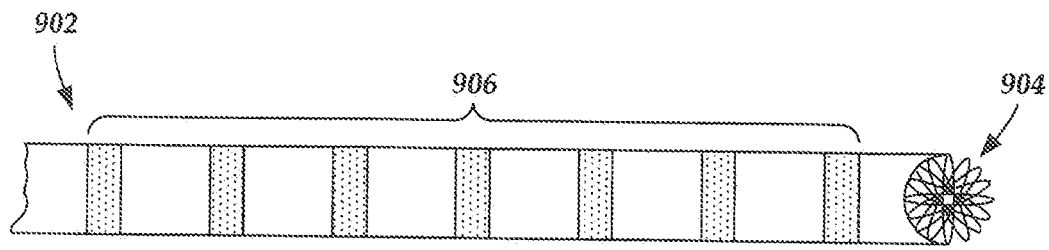
FIG. 9A is a schematic side view of one embodiment of a distal portion of a lead with an expandable sphere disposed in an undeployed position on the lead distal to a plurality of electrodes, according to the invention.

In some embodiments, an anchoring unit disposed on a lead includes a tip that may expand. FIG. 9A is a schematic side view of one embodiment of a distal portion of a lead 902 that includes a tip 904 that may expand disposed in an undeployed position on the lead 902 distal to a plurality of electrodes 906. In at least some embodiments, the lead 902 can be positioned while the tip 904 is in an undeployed position. Once the lead 902 is positioned, the tip 904 can be transitioned to a deployed position by expanding the tip 904. In at least some embodiments, the tip 904 is permanently or removably coupled to a distal tip of the lead 902. In at least some embodiments, a stylet disposed in a lumen defined in the lead 902 may be used to push against the tip 904, causing the tip 904 to expand.

Figure 9B:
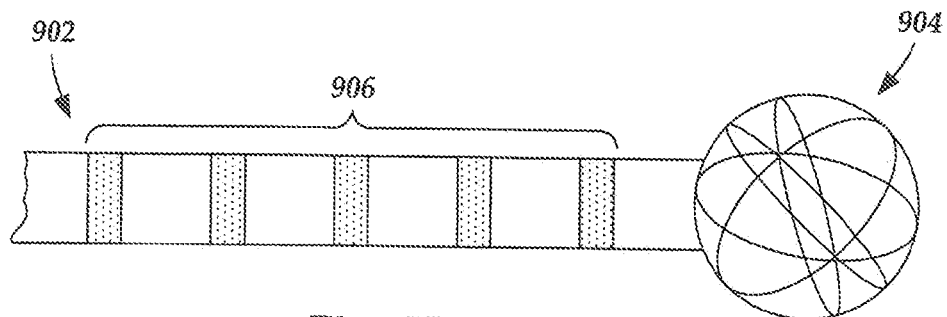
FIG. 9B is a schematic side view of one embodiment of a distal portion of the lead shown in FIG. 9A with an expandable sphere disposed in a deployed position on the lead distal to a plurality of electrodes, according to the invention.

FIG. 9B is a schematic side view of one embodiment of a distal portion of the lead 902 including a tip 904 disposed in a deployed position on the lead 902 distal to the plurality of electrodes 906. In at least some embodiments, the tip 904 is configured and arranged to maintain a deployed position and may be implanted using a lead introducer disposed over the tip 904 in a manner similar to the lead 402 shown in FIG. 4C. In alternate embodiments, the tip 904 may also be contractible, so that the tip 904 can transition from a deployed position to an undeployed position.

Figure 9C:
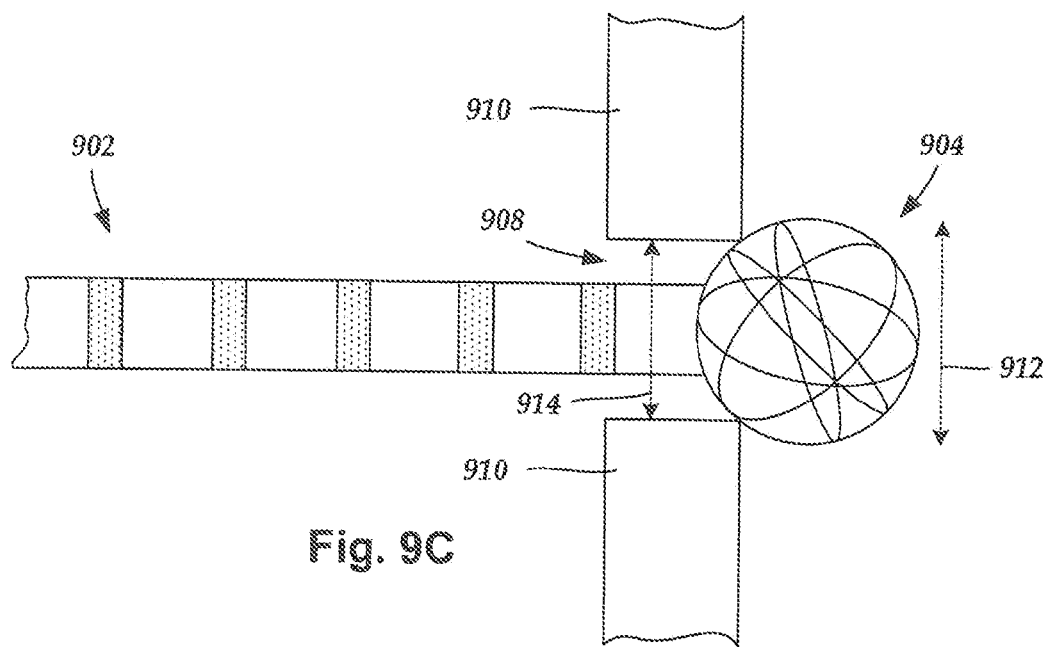
FIG. 9C is a schematic side view of one embodiment of a distal portion of the lead shown in FIG. 9A extending through a foramen of a sacrum and anchored to the sacrum by an expandable sphere disposed in a deployed position on the lead distal to a plurality of electrodes, according to the invention.

In at least some embodiments, the tip 904 can be used to anchor the lead 902 to a bony structure. FIG. 9C is a schematic side view of one embodiment of the distal portion of the lead 902 extending through a foramen 908 of a bony structure 910 and anchored to the bony structure 910 by the tip 904 disposed in a deployed position on the distal portion of the lead 902. As shown in FIG. 9C, the lead 902 extends through the foramen 908 of the bony structure 908 and the tip 904 is in a deployed position on an opposite side of the foramen 908 from a proximal end (not shown) of the lead 902. The tip 904 has a diameter, shown in FIG. 9C as a two-headed dotted arrow 912, and the foramen 908 has a diameter, shown in FIG. 9C as a two-headed dotted arrow 914. The diameter 912 of the tip 904 is greater in length than the diameter 914 of the foramen 908. Thus, the sphere 904 prevents the lead 902 from migrating back through the foramen 908. In alternate embodiments, the tip 904 is placed in a deployed position within the foramen 908 to anchor the lead 902 to the foramen 908. In yet other embodiments, the tip 904 is placed in a deployed position to anchor the lead 902 against cartilage or soft tissue. In at least some embodiments, the diameter of the tip 904 in a deployed position is greater than the lead 902, but less than the foramen 908. It will be understood that prevention of migration of the lead 902 may also occur when the diameter of the tip 904 in a deployed position is greater than the lead 902, but less than the diameter of the foramen 908. Note that, in some circumstances it may be undesirable for the diameter of the tip 904 in a deployed position to have a diameter that is less than the diameter of the foramen 908 so as to reduce the risk of damaging soft tissue extending through the foramen 908.

Figure 10A:
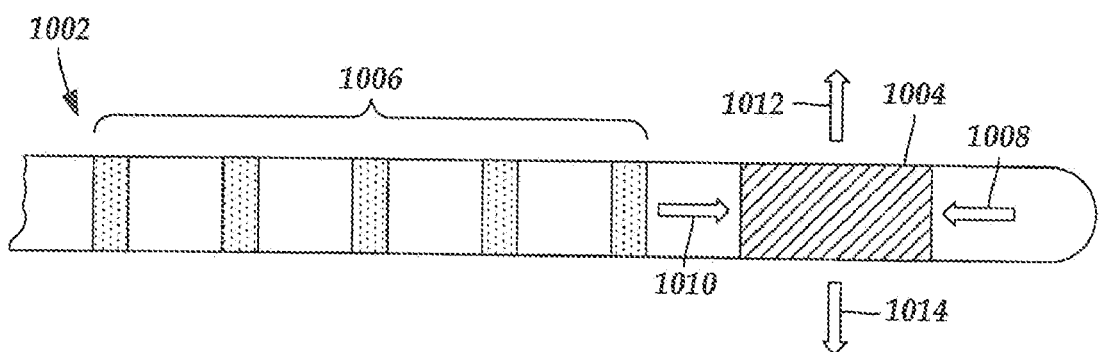
FIG. 10A is a schematic side view of one embodiment of a distal portion of a lead with a section of deformable material disposed in an undeployed position on the lead distal to a plurality of electrodes, according to the invention.

In some embodiments, an anchoring unit disposed on a lead includes one or more sections of deformable material disposed on a lead. FIG. 10A is a schematic side view of one embodiment of a distal portion of a lead 1002 that includes a section of deformable material 1004 disposed in an undeployed position on the lead 1004 distal to a plurality of electrodes 1006. The section of deformable material 1004 may be formed in a number of different shapes. For example, the deformable material 1004 may be cylindrical, O-ring-shaped, gasket-shaped, annulus-shaped, and the like. The deformable material 1004 may be formed by, a pliable, reformable, biocompatible material including, for example, rubber, and the like. In at least some embodiments, the deformable material 1004 is sandwiched between materials less deformable than the deformable material 1004.

In at least some embodiments, when the deformable material 1004 is longitudinally compressed, the deformable material 1004 expands radially. For example, when a portion of the lead 1002 distal to the deformable material is moved relative to the remaining portion of the lead 1002 in a direction shown by directional arrow 1008, or the portion of the lead proximal to the deformable material is moved relative to the remaining portion of the lead 1002 in a direction shown by directional arrow 1010, the deformable material may expand in one or more radial directions approximately orthogonal to a longitudinal length of the lead 1002, such as the directions shown by directional arrows 1012 and 1014.

Figure 10B:
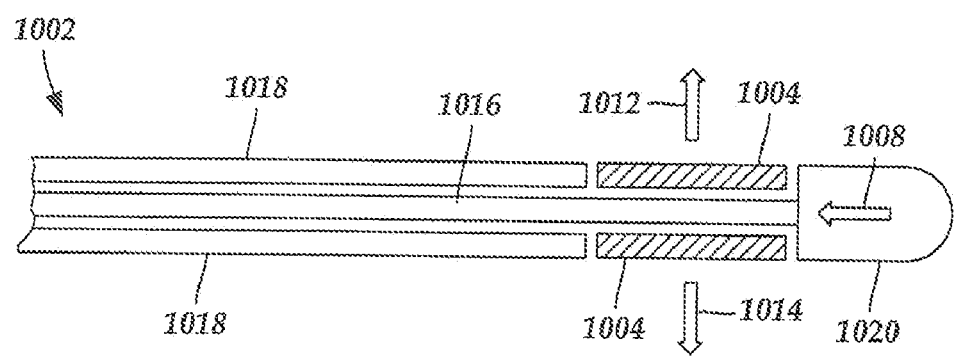
FIG. 10B is a schematic longitudinal cross-sectional view of one embodiment of the lead shown in FIG. 10A, the lead including an inner section that may be used to compress deformable material between a distal tip and an outer section of the lead, according to the invention.

In at least some embodiments, the lead 1002 may include a movable inner section that may be used to compresses the deformable material 1004 between a distal tip and stationary outer section. FIG. 10B is a schematic longitudinal cross-sectional view of one embodiment of the distal portion of the lead 1002. The lead 1002 includes a movable inner section 1016, a stationary outer section 1018, a distal tip 1020, and the deformable material 1004. In at least some embodiments, the distal tip 1020 is coupled to distal end of the movable inner section 1016. In at least some embodiments, the inner section 1004 is a stylet. When the inner section 1016 is moved in a direction as shown by directional arrow 1008, the deformable material 1004 may be compressed between the distal tip 1020 and the stationary outer section 1018, causing the deformable material 1004 to expand in one or more radial directions approximately orthogonal to a longitudinal length of the lead 1002, such as the directions shown by directional arrows 1012 and 1014. In at least some embodiments, one or more stops may be used to removably or permanently maintain the deformable material 1004 in a compressed (deployed) position.

Figure 10C:
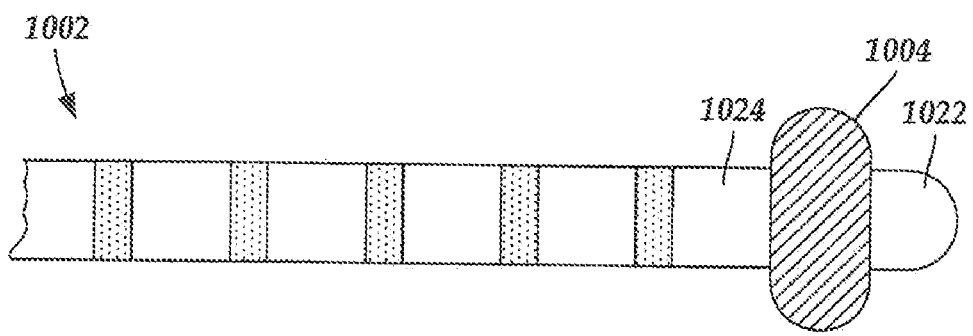
FIG. 10C is a schematic side view of one embodiment of a distal portion of the lead shown in FIG. 10A with a section of deformable material disposed on the lead distal to a plurality of electrodes and with a portion of the lead distal to the deformable material longitudinally compressed to radially expand the deformable material into a deployed position, according to the invention.

FIG. 10C is a schematic side view of one embodiment of a distal portion of the lead 1002 longitudinally compressed, thereby causing the deformable material 1004 to radially expand. In at least some embodiments, the portion 1022 of the lead 1002 distal to the deformable material 1004 is moved proximally relative to the remaining portion of the lead 1002 by screwing or pulling the portion 1022 of the lead 1002 distal to the deformable material 1004 relative to the remaining portions of the lead 1002. In at least some embodiments, the portion 1024 of the lead 1002 proximal to the deformable material 1004 is moved distally relative to the remaining portion of the lead 1002 by screwing or pulling the portion 1024 of the lead 1002 proximal to the deformable material 1004 relative to the remaining portions of the lead 1002. In at least some embodiments, both the portion 1022 of the lead 1002 distal to the deformable region 1004 and the portion 1022 of the lead 1002 proximal to the deformable region 1004 are pulled or screwed longitudinally inward to longitudinally compress the deformable region 1004.

Figure 10D:
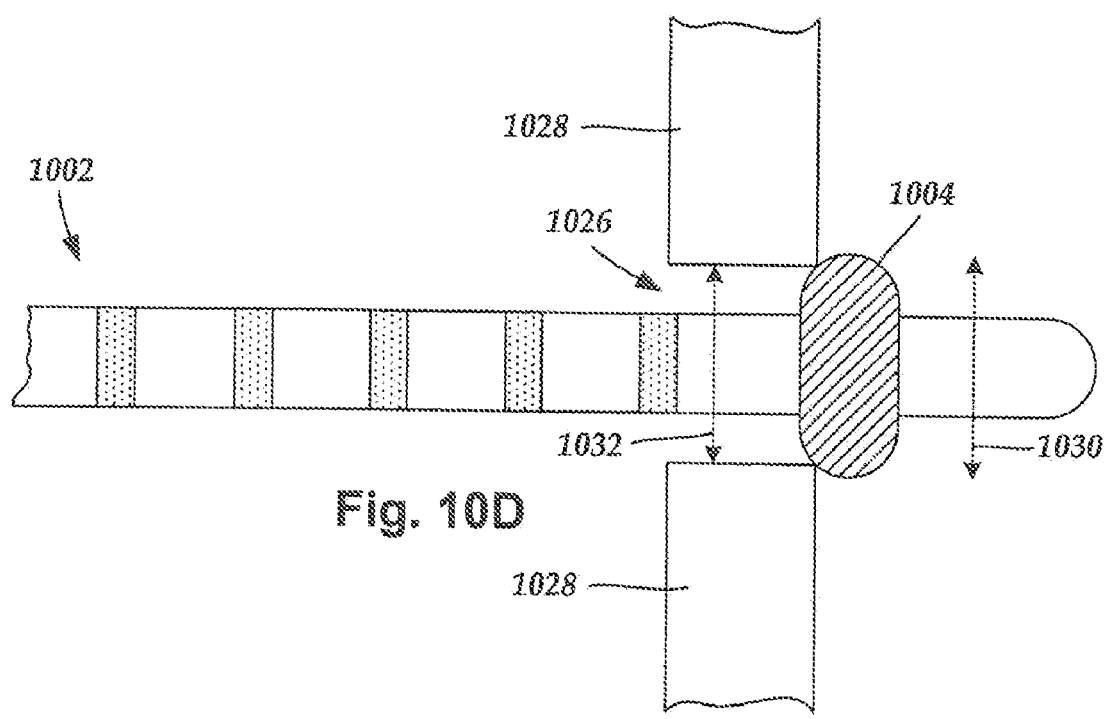
FIG. 10D is a schematic side view of one embodiment of a distal portion of the lead shown in FIG. 10A extending through a foramen of a sacrum and anchored to the sacrum by a section of deformable material disposed in a deployed position on the lead distal to a plurality of electrodes, according to the invention.

In at least some embodiments, the section of deformable material 1004 disposed at the distal end of the lead 1002 can be used to anchor the lead 1002 to a bony structure or to soft tissue. FIG. 10D is a schematic side view of one embodiment of the distal portion of the lead 1002 extending through a foramen 1026 of a bony structure 1028 and anchored to the bony structure 1028 by the deformable material 1004 disposed in a deployed position on the distal portion of the lead 1002. As shown in FIG. 10D, the lead 1002 extends through the foramen 1026 of the bony structure 1028 and the section of deformable material 1004 is in a deployed position on an opposite side of the bony structure 1028 from a proximal end (not shown) of the lead 1002. The deformable material 1004 has a diameter, shown in FIG. 10D as a two-headed dotted arrow 1030, and the foramen 1026 has a diameter, shown in FIG. 10D as a two-headed dotted arrow 1032. The diameter 1030 of the deformable material 1004 is greater in length than the diameter 1032 of the foramen 1026. Thus, the deformable material 1004 prevents the lead 1002 from migrating back through the foramen 1026. In alternate embodiments, the deformable material 1004 is placed in a deployed position within the foramen 1026 to anchor the lead 1004 to the foramen 1026. In yet other embodiments, the deformable material 1004 is placed in a deployed position to anchor the lead 1002 against cartilage or soft tissue. In at least some embodiments, the diameter of the deformable material 1004 in a deployed position is greater than the lead 1002, but less than the foramen 1026. It will be understood that prevention of migration of the lead 1002 may also occur when the diameter of the deformable material 1004 in a deployed position is greater than the lead 1002, but less than the diameter of the foramen 1026. Note that, in some circumstances it may be undesirable for the diameter of the deformable material 1004 to have a diameter in a deployed position that is less than the diameter of the foramen 1026 so as to reduce the risk of damaging soft tissue extending through the foramen 1026.

Figure 10E:
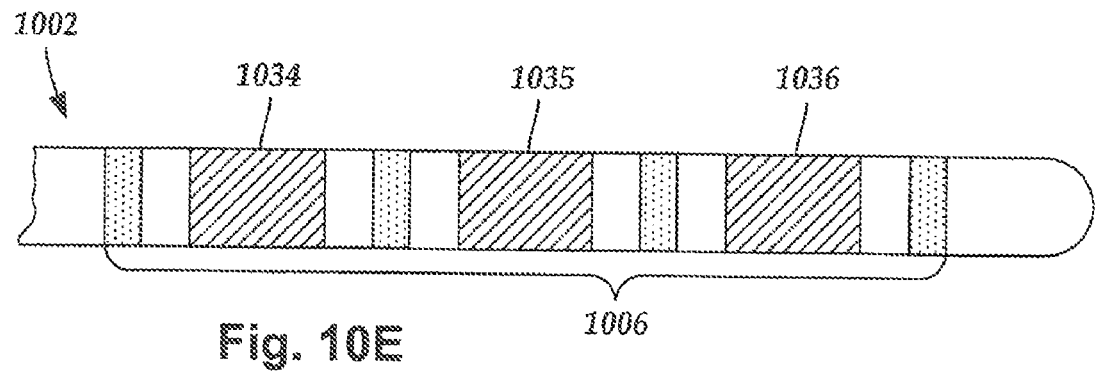
FIG. 10E is a schematic side view of one embodiment of a distal portion of a lead with sections of deformable material disposed on the lead in undeployed positions between adjacent electrodes, according to the invention.

In at least some embodiments, more than one section of deformable material 1004 can be disposed on the lead 1002 distal to the electrodes 1006. In at least some embodiments, one or more sections of deformable material 1004 can be disposed along other portions of the lead 1002. For example, the one or more sections of deformable material 1004 may be disposed between adjacent electrodes 1006, or on a portion of the lead 1002 proximal to the electrodes 1006. FIG. 10E is a schematic side view of one embodiment of a distal portion of the lead 1002. The lead 1002 includes sections of deformable material 1034-1036 disposed on the lead 1002 in undeployed positions between electrodes 1006. In some embodiments, a single section of deformable material 1034-1036 is disposed between two adjacent electrodes 1006. In other embodiments, more than one section of deformable material 1034-1036 is disposed between electrodes 1006.

Figure 10F:
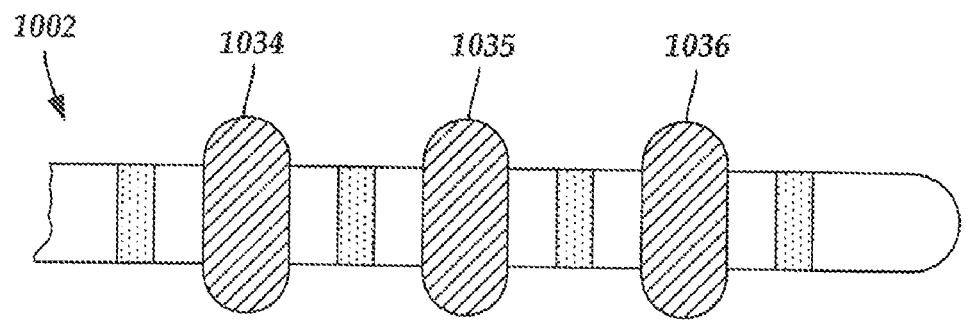
FIG. 10F is a schematic side view of one embodiment of a distal portion of the lead shown in FIG. 10E with longitudinally compressed sections of deformable material disposed between adjacent electrodes, the longitudinally compressed sections of deformable material radially expanded into deployed positions, according to the invention.

In at least some embodiments, the deformable material 1034-1036 can be longitudinally compressed, thereby causing the deformable material 1034-1036 to radially expand in a manner similar to the method of longitudinally compressing the deformable material 1004 discussed above, with reference to FIGS. 10A and 10B. FIG. 10F is a schematic side view of one embodiment of a distal portion of the lead 1002 longitudinally compressing sections of deformable material 1034-1036 to radially expand the sections of deformable material 1034-1036 into deployed positions.

Figure 10G:
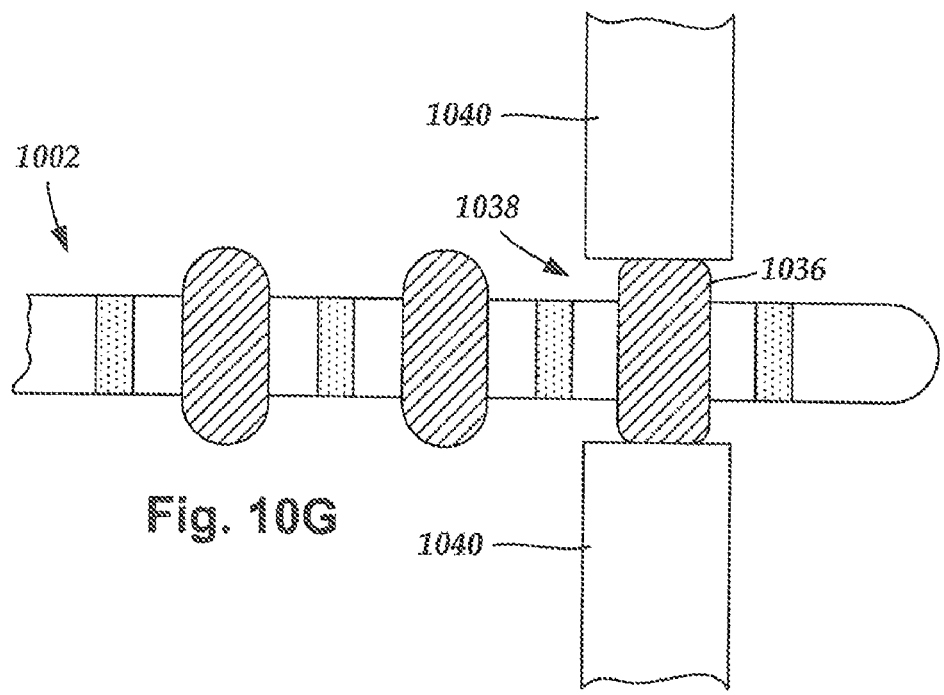
FIG. 10G is a schematic side view of one embodiment of a distal portion of the lead shown in FIG. 10E anchored to a foramen of a sacrum by a section of longitudinally compressed and radially expanded deformable material disposed on the lead between two adjacent electrodes, according to the invention.

In at least some embodiments, one or more of the sections of deformable material 1034-1036 disposed between electrodes on the lead 1002 can be used to anchor the lead 1002 to a bony structure or soft tissue. FIG. 10G is a schematic side view of one embodiment of the lead 1002 extending through a foramen 1038 of a bony structure 1040 and anchored to the walls of the foramen 1038 by the section of deformable material 1036 disposed in a deployed position on the distal portion of the lead 1002. In some embodiments, one or more of the sections of deformable material 1034-1036 are in a deployable position. In alternate embodiments, each of the sections of deformable material 1034-1036 is in a deployed position.

In other embodiments, one or more of the sections of deformable material 1034-1036 disposed between the electrodes is placed in a deployed position on the opposite side of the bony structure 1040 from a proximal end (not shown) of the lead 1002, in a similar manner as shown in FIG. 10D. In yet other embodiments, one or more of the sections of the deformable material 1034-1036 is placed in a deployed position to anchor the lead 1002 against cartilage or soft tissue. In at least some embodiments, the diameter of one or more sections of deformable material 1034-1036 in deployed positions is greater than the lead 1002, but less than the foramen 1038. It will be understood that prevention of migration of the lead 1002 may also occur when the diameter of one or more sections of deformable material 1034-1036 in deployed positions is greater than the lead 1002, but less than the diameter of the foramen 1038. Note that, in some circumstances it may be undesirable for the diameter of one or more sections of the deformable material 1034-1036 in deployed positions to have diameters that are less than the diameter of the foramen 1038 so as to reduce the risk of damaging soft tissue extending through the foramen 1038.

In at least some embodiments, a plurality of anchoring units can be used to anchor a lead. In at least some embodiments, a plurality of different types of anchoring units disposed on one or more different locations on the lead may be used to anchor a lead. For example, a lead may include both one or more tines and one or more sections of deformable materials. In another example, a lead may include one or tines, an expandable tip, and a spring. In at least some embodiments, an anchoring unit is at least partially formed from, or coated by, one or more porous materials configured and arranged to facilitate integration of the anchoring unit to at least one bony structure, such as a sacrum.

Figure 11:
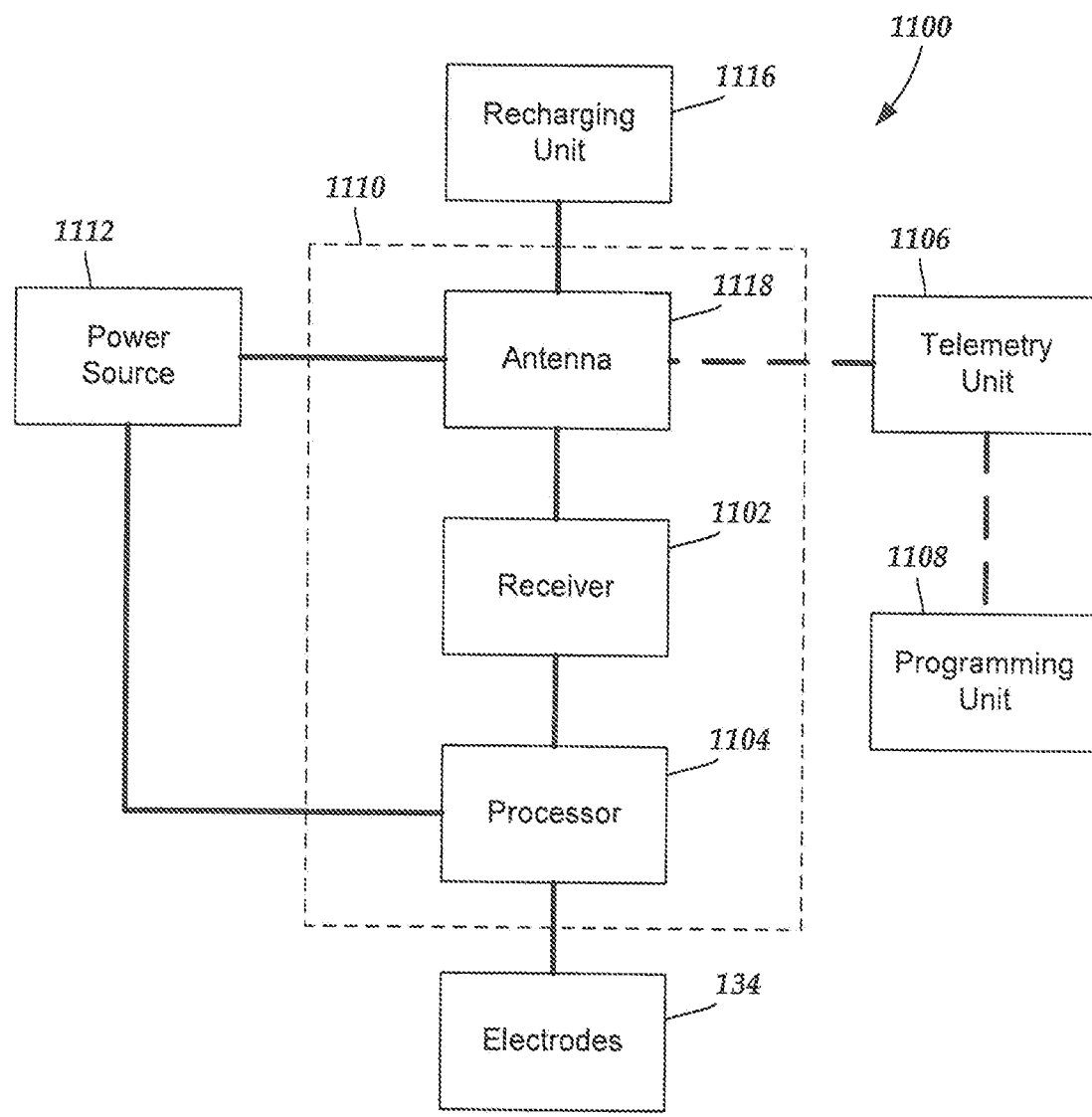
FIG. 11 is a schematic overview of one embodiment of components of a stimulation system, including an electronic subassembly disposed within a control module, according to the invention.

FIG. 11 is a schematic overview of one embodiment of components of an electrical stimulation system 1100 including an electronic subassembly 1110 disposed within a control module. It will be understood that the electrical stimulation system can include more, fewer, or different components and can have a variety of different configurations including those configurations disclosed in the stimulator references cited herein.

Some of the components (for example, power source 1112, antenna 1118, receiver 1102, and processor 1104) of the electrical stimulation system can be positioned on one or more circuit boards or similar carriers within a sealed housing of an implantable pulse generator, if desired. Any power source 1112 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 1118 or a secondary antenna. The external power source can be in a device that is mounted on the skin of the user or in a unit that is provided near the user on a permanent or periodic basis.

If the power source 1112 is a rechargeable battery, the battery may be recharged using the optional antenna 1118, if desired. Power can be provided to the battery for recharging by inductively coupling the battery through the antenna to a recharging unit 1116 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1104 is generally included to control the timing and electrical characteristics of the electrical stimulation system. For example, the processor 1104 can, if desired, control one or more of the timing, frequency, strength, duration, and waveform of the pulses. In addition, the processor 1104 can select which electrodes can be used to provide stimulation, if desired. In some embodiments, the processor 1104 may select which electrode(s) are cathodes and which electrode(s) are anodes. In some embodiments, the processor 1104 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1108 that, for example, allows modification of pulse characteristics. In the illustrated embodiment, the processor 1104 is coupled to a receiver 1102 which, in turn, is coupled to the optional antenna 1118. This allows the processor 1104 to receive instructions from an external source to, for example, direct the pulse characteristics and the selection of electrodes, if desired.

In one embodiment, the antenna 1118 is capable of receiving signals (e.g., RF signals) from an external telemetry unit 1106 which is programmed by a programming unit 1108. The programming unit 1108 can be external to, or part of, the telemetry unit 1106. The telemetry unit 1106 can be a device that is worn on the skin of the user or can be carried by the user and can have a form similar to a pager, cellular phone, or remote control, if desired. As another alternative, the telemetry unit 1106 may not be worn or carried by the user but may only be available at a home station or at a clinician's office. The programming unit 1108 can be any unit that can provide information to the telemetry unit 1106 for transmission to the electrical stimulation system 1100. The programming unit 1108 can be part of the telemetry unit 1106 or can provide signals or information to the telemetry unit 1106 via a wireless or wired connection. One example of a suitable programming unit is a computer operated by the user or clinician to send signals to the telemetry unit 1106.

The signals sent to the processor 1104 via the antenna 1118 and receiver 1102 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1100 to cease operation, to start operation, to start charging the battery, or to stop charging the battery. In other embodiments, the stimulation system does not include an antenna 1118 or receiver 1102 and the processor 1104 operates as programmed.

Optionally, the electrical stimulation system 1100 may include a transmitter (not shown) coupled to the processor 1104 and the antenna 1118 for transmitting signals back to the telemetry unit 1106 or another unit capable of receiving the signals. For example, the electrical stimulation system 1100 may transmit signals indicating whether the electrical stimulation system 1100 is operating properly or not or indicating when the battery needs to be charged or the level of charge remaining in the battery. The processor 1104 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A nerve stimulation lead comprising:
   a lead body with a distal end, a proximal end, and a longitudinal length;
   a plurality of electrodes disposed at the distal end;
   a plurality of terminals disposed at the proximal end;
   a plurality of conductive wires electrically coupling the plurality of electrodes electrically to the plurality of terminals; and
   a plurality of anchoring units configured and arranged for anchoring the nerve stimulation lead against a bony structure or against soft tissue abutting a bony structure, each of the plurality of anchoring units is configured and arranged to transition between an undeployed position and a deployed position, the undeployed position facilitating positioning of the nerve stimulation lead and the deployed position facilitating anchoring of the nerve stimulation lead, wherein, in the undeployed position, each anchoring unit is disposed within the lead body and, in the deployed position, each anchoring units extends from the lead body.

2. The nerve stimulation lead of claim 1, wherein the plurality of anchoring units comprises at least two tines disposed on the nerve stimulation lead.

3. The nerve stimulation lead of claim 1, wherein the plurality of anchoring units are configured and arranged to transition from the undeployed position to the deployed position by twisting at least a portion of the nerve stimulation lead.

4. The nerve stimulation lead of claim 3, wherein the plurality of anchoring units are configured and arranged to return to the undeployed position when at least a portion of the lead is twisted in a direction opposite that used to deploy the at least one anchoring unit.

5. The nerve stimulation lead of claim 1, wherein the plurality of anchoring units comprise a first anchoring unit and a second anchoring unit and the first and second anchoring units are disposed on the stimulation lead between different pairs of the plurality of electrodes.

6. The nerve stimulation lead of claim 1, wherein the plurality of anchoring units comprise a plurality of tines arranged in a plurality of spaced-apart rings.

7. An electrical stimulating system comprising:
   the nerve stimulation lead of claim 1; and
   a control module configured and arranged to electrically couple to the proximal end of the nerve stimulation lead, the control module comprising
      a housing, and
      an electronic subassembly disposed in the housing; and
   a connector for receiving the nerve stimulation lead, the connector having a proximal end and a distal end, the connector configured and arranged to receive the nerve stimulation lead, the connector comprising
      a connector housing defining a port at the distal end of the connector, the port configured and arranged for receiving the proximal end of the nerve stimulation lead, and
      a plurality of connector contacts disposed in the connector housing, the connector contacts configured and arranged to couple to at least one of the plurality of terminals disposed on the proximal end of the lead body.

8. A method of stimulating tissue, the method comprising:
   implanting a nerve stimulation lead near tissue to be stimulated, the nerve stimulation lead comprising a plurality of electrodes disposed at a distal end of the nerve stimulation lead; a plurality of terminals disposed at a proximal end of the nerve stimulation lead; a plurality of conductive wires electrically coupling the plurality of electrodes electrically to the plurality of terminals; and at least one anchoring unit disposed on the nerve stimulation lead, wherein during implantation the at least one anchoring unit is in an undeployed position;
   deploying the at least one anchoring unit by twisting at least a portion of the nerve stimulation lead;
   anchoring the nerve stimulation lead against a bony structure or against soft tissue abutting a bony structure using the at least one anchoring unit that has been deployed; and
   stimulating the tissue using a current provided through at least one of the plurality of electrodes.

9. The method of claim 8, wherein anchoring the nerve stimulation lead comprises anchoring the nerve stimulation lead to a wall of a foramen of the bony structure or to soft tissue extending along the wall of the foramen.

10. The method of claim 8, wherein anchoring the nerve stimulation lead comprises anchoring the nerve stimulation lead in proximity to a foramen of the bony structure through which the distal end of the nerve stimulation lead at least partially extends.

11. The method of claim 8, wherein anchoring the nerve stimulation lead comprises anchoring the nerve stimulation lead against a first side of the bony structure in proximity to a foramen through which the distal end of the nerve stimulation lead at least partially extends, the first side of the bony structure being opposite to a side of the bony structure through which the distal end of the nerve stimulation lead entered the foramen.

12. The method of claim 8, wherein the at least one anchoring unit comprises at least two deployable tines disposed on the nerve stimulation lead.

13. The method of claim 12, wherein each tine has an undeployed position in which it lies against the lead and a deployed position in which it projects outward from the lead.

14. The method of claim 13, further comprising returning the at least two deployable tines to the undeployed position by twisting at least a portion of the lead in a direction opposite that used in deploying the at least two deployable tines.

15. The method of claim 13, wherein, once deployed, the at least two deployable tines are configured and arranged to remain in the deployed position even if at least a portion of the lead is rotated in a direction opposite that used in deploying the at least two deployable tines.

16. The method of claim 8, wherein that at least one anchoring unit comprises a spring having a deployed position and an undeployed position, the spring having higher potential energy in the undeployed position than in the deployed position.

17. The method of claim 8, wherein deploying the at least one anchoring unit comprises deploying the at least one anchoring unit from at least one annular groove formed in the nerve stimulation lead by twisting at least the portion of the nerve stimulation lead.

18. A method of stimulating tissue, the method comprising:
   implanting a nerve stimulation lead near tissue to be stimulated, the nerve stimulation lead comprising a plurality of electrodes disposed at a distal end of the nerve stimulation lead; a plurality of terminals disposed at a proximal end of the nerve stimulation lead; a plurality of conductive wires electrically coupling the plurality of electrodes electrically to the plurality of terminals; and at least one anchoring unit disposed on the nerve stimulation lead, wherein at least one of the anchoring units comprises an expandable tip disposed on the nerve stimulation lead distal to the plurality of electrodes, wherein during implantation the expandable tip is in an undeployed position;

deploying the expandable tip by pushing against the undeployed expandable tip using a stylet disposed within the nerve stimulation lead;

anchoring the nerve stimulation lead against a bony structure or against soft tissue abutting a bony structure using the deployed expandable tip; and stimulating the tissue using a current provided through at least one of the plurality of electrodes.

\* \* \* \* \*